United States Patent
Barbagallo et al.

(10) Patent No.: US 8,420,651 B2
(45) Date of Patent: Apr. 16, 2013

(54) SUBSTITUTED 1-ALKYLCINNOLIN-4(1H)-ONE DERIVATIVES, PREPARATION THEREOF AND THERAPEUTIC APPLICATION OF SAME

(75) Inventors: Elodie Barbagallo, Paris (FR); Carole Legeay, Paris (FR); Murielle Rinaldi-Carmona, Paris (FR); Pascale Roux, Paris (FR); Claude Vernhet, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/262,869

(22) PCT Filed: Apr. 6, 2010

(86) PCT No.: PCT/FR2010/050657
§ 371 (c)(1),
(2), (4) Date: Feb. 3, 2012

(87) PCT Pub. No.: WO2010/116084
PCT Pub. Date: Oct. 14, 2010

(65) Prior Publication Data
US 2012/0129864 A1    May 24, 2012

(30) Foreign Application Priority Data
Apr. 7, 2009  (FR) ..................... 09 01696

(51) Int. Cl.
*A61K 31/50* (2006.01)
*A61K 31/501* (2006.01)

(52) U.S. Cl.
USPC .................. 514/252.01; 544/237; 544/238

(58) Field of Classification Search ............... 544/235, 544/237, 238; 514/248, 252.01
See application file for complete search history.

(56) References Cited

FOREIGN PATENT DOCUMENTS
WO    WO2009/053799 A1    4/2009

OTHER PUBLICATIONS

Stern et al., J. Med. Chem, 2007. 50. 5471-5484*

Buttero et al, Synthesis (1986) 12, 1059-61.*
Lowrie, Harman S., Journal of Medicinal Chemistry (1966), 9(5), 784-6CODEN: JMCMAR; ISSN: 0022-2623.*
McMahon et al.*
Pinedo et al.*
Stern, Eric et al., "Pharmacomodulations around the 4-Oxo-1,4-dihydroquinoline-3-carboxamides, a Class of Potent CB2-Selective Cannabinoid Receptor Ligands: Consequences in Receptor Affinity and Functionality," Journal of Medicinal Chemistry (2007), vol. 50, pp. 5471-5484.
Lowrie, H.S., "3-Phenylcinnolines. III. Derivatives of Hydroxy-3-phenylcinnolines," Journal of Medicinal Chemistry (1966), vol. 9, No. 5, pp. 784-786.
Del Buttero, Paola et al., "A Convenient Synthesis of 1-Alkyl-4-oxo-1,4-dihydrocinnolines," Synthesis (1986), pp. 1059-1061.
International Search Report dated Jul. 26, 2010 issued in PCT/FR2010/050657.

* cited by examiner

*Primary Examiner* — Paul V. Ward
(74) *Attorney, Agent, or Firm* — Scully, Scott, Murphy & Presser, P.C.

(57) ABSTRACT

The subject of the present invention is compounds corresponding to the formula (I) in which: X represents a divalent $(C_2-C_5)$alkylene radical which is unsubstituted or substituted one or more times by an Alk group; $R_1$ represents a phenyl, a naphthyl, a pyridyl, a 1-benzothienyl or a 1,3-benzodioxolyl; $R_2$ represents a hydrogen atom, a halogen atom, an Alk group, an OAlk group or else a group chosen from —S-Alk, —SO-Alk, —SO$_2$-Alk, —CO—N($R_4$)-Alk, —N($R_4$)SO$_2$-Alk, —N($R_4$)CO-Alk, —N($R_4$)SO$_2$—N(Alk)$_2$; $R_3$ represents a hydrogen atom, a halogen atom, an Alk group or an OAlk group; $R_4$ represents a hydrogen atom or a $(C_1-C_4)$alkyl; Alk represents an unsubstituted or substituted $(C_1-C_4)$alkyl. Preparation process and therapeutic application.

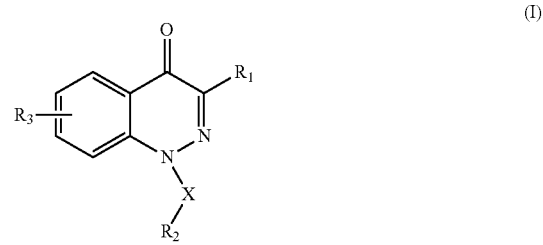

8 Claims, No Drawings

SUBSTITUTED 1-ALKYLCINNOLIN-4(1H)-ONE DERIVATIVES, PREPARATION THEREOF AND THERAPEUTIC APPLICATION OF SAME

A subject-matter of the present invention is novel 1-alkylcinnolin-4(1H)-one derivatives having an affinity for type 2 cannabinoid ($CB_2$) receptors, their preparation and their therapeutic application.

$\Delta^9$-THC is the main active constituent extracted from *Cannabis sativa* [Paton, Annual Review in Pharmacology (1975) 15, 191-220].

Numerous papers have described not only psychotropic effects of cannabinoids but also an influence of the latter on the immune function [Klein et al., Immunology Today (1998) 19, 373-381], the control of pain [Pertwee, Progress in Neurobiology (2001) 63, 569-611], food intake [Cota et al., International Journal of Obesity (2003) 27, 289-301] and many other biological functions [Nahas et al., Marihuana and Medicine (1999), Humana Press: Totowa, N.J., USA].

The effects of cannabinoids are due to interaction with specific high-affinity G protein-coupled receptors present at the central and peripheral level [Howlett et al., Pharmacological Reviews (2002) 54, 161-2002].

The central effects of cannabinoids concern a first type of receptor ($CB_1$) present mainly in the brain but also in the periphery [Matsuda et al., Nature (1990) 346, 561-564]. Furthermore, Munro et al. [Nature (1993) 365, 61-65] cloned a second type of cannabinoid receptor referred to as $CB_2$, which is present in the periphery and in particular in the cells of the immune system but also in the brain in some pathological conditions.

Some indole derivatives have been cited in the prior art as exhibiting an affinity for $CB_2$ receptors; mention may be made of patent applications U.S. Pat. No. 5,532,237, EP 833 818, U.S. Pat. No. 4,581,354, WO 2002/42269, WO 2003/097597, WO 2006/069196 and WO 2007/057571.

Cinnoline derivatives have been described by E. Stern et al. in J. Med. Chem., 2007, 50, 5471-5484, in particular the compound of formula:

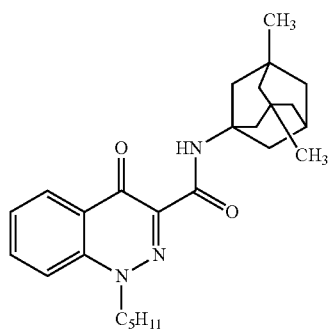

(1)

Novel 1-alkylcinnolin-4(1H)-one derivatives have now been found which exhibit a high affinity and a high selectivity for cannabinoid $CB_2$ receptors. These compounds have a modulatory effect on the activity of $CB_2$ receptors. Modulatory effect is understood in particular to mean agonist, antagonist and/or inverse agonist effects.

A subject-matter of the present invention is compounds corresponding to the formula (I):

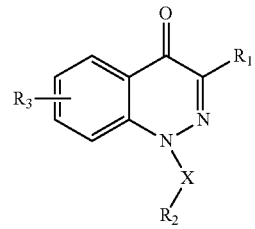

(I)

in which:
X represents a divalent ($C_2$-$C_5$)alkylene radical which is unsubstituted or substituted one or more times by an Alk group;
$R_1$ represents:
  a phenyl which is substituted one or more times by substituents chosen independently from a halogen atom, an Alk group, an OAlk group, a cyano or an —$NHSO_2$Alk group;
  a naphthyl which is unsubstituted or substituted one or more times by substituents chosen independently from a halogen atom, an Alk group or an OAlk group;
  a pyridyl which is unsubstituted or substituted one or more times by substituents chosen independently from a halogen atom, an Alk group or an OAlk group;
  a 1-benzothienyl which is unsubstituted or substituted one or more times by substituents chosen independently from a halogen atom, an Alk group or an OAlk group;
  a 1,3-benzodioxolyl which is unsubstituted or substituted one or more times by substituents chosen independently from a halogen atom, an Alk group or an OAlk group;
$R_2$ represents a hydrogen atom, a halogen atom, an Alk group, an OAlk group or also a group chosen from —S-Alk, —SO-Alk, —$SO_2$-Alk, —CO—N($R_4$)-Alk, —N($R_4$)$SO_2$-Alk, —N($R_4$)CO-Alk or —N($R_4$)$SO_2$—N(Alk)$_2$;
$R_3$ represents a hydrogen atom, a halogen atom, an Alk group or an OAlk group;
$R_4$ represents a hydrogen atom or a ($C_1$-$C_4$)alkyl;
Alk represents a ($C_1$-$C_4$)alkyl which is unsubstituted or substituted one or more times by a fluorine atom.

The compounds of formula (I) can comprise one or more asymmetric carbon atoms. They can thus exist in the form of enantiomers or of diastereoisomers. These enantiomers and diastereoisomers, and their mixtures, including racemic mixtures, come within the invention.

The compounds of formula (I) can exist in the form of bases or of addition salts with acids. Such addition salts come within the invention.

These salts are advantageously prepared with pharmaceutically acceptable acids but the salts of other acids of use in the purification or the isolation of the compounds of formula (I) also come within the invention.

When the compounds of formula (I) comprise a sulphur atom, all the optical isomers and their mixtures in any proportions are subject-matters of the invention.

($C_2$-$C_5$)alkylene is understood to mean a divalent radical of 2 to 5 carbon atoms, such as the ethylene, trimethylene, tetramethylene or pentamethylene radical.

($C_1$-$C_4$)Alkyl is understood to mean a linear or branched alkyl radical of 1 to 4 carbon atoms, such as the methyl, ethyl, propyl, isopropyl, n-butyl, isobutyl, sec-butyl or tert-butyl radical.

(C₁-C₄)Alkoxy is understood to mean an oxygen atom bonded to a linear or branched carbon-comprising radical of 1 to 4 carbon atoms, such as the methoxy, ethoxy, propoxy, isopropoxy, butoxy, isobutoxy, sec-butoxy or tert-butoxy radical.

Halogen atom is understood to mean a bromine, chlorine, fluorine or iodine atom.

Singled out among the compounds of formula (I) which are subject-matters of the invention are the compounds for which:

X represents a divalent $(C_2-C_5)$alkylene radical which is unsubstituted or substituted one or more times by an Alk group;

$R_1$ represents:
  a phenyl which is substituted one or more times by substituents chosen independently from a halogen atom, an Alk group or an OAlk group;
  a pyridyl which is substituted one or more times by substituents chosen independently from a halogen atom or an Alk group;

$R_2$ represents a hydrogen atom, a halogen atom, an Alk group, an OAlk group, an —S-Alk group, an —SO-Alk group, an —SO₂-Alk group, a —CO—N(R₄)-Alk group, an —N(R₄)SO₂-Alk group, an —N(R₄)CO-Alk group or an —N(R₄)—SO₂—N(Alk)₂ group;

$R_3$ represents a hydrogen atom, a halogen atom, an Alk group or an OAlk group;

$R_4$ represents a hydrogen atom or a $(C_1-C_4)$alkyl;

Alk represents a $(C_1-C_4)$alkyl which is unsubstituted or substituted one or more times by a fluorine atom;

in the form of the base or of an addition salt with an acid.

Preference is particularly given to the compounds of formula (I) in which:

X represents a divalent $(C_2-C_5)$alkylene radical which is unsubstituted or substituted one or more times by a methyl;

$R_1$ represents: 3-fluoro-2-trifluoromethylphenyl, 2-fluoro-3-trifluoromethylphenyl, 3-trifluoromethoxyphenyl, 2-chloro-3-trifluoromethylphenyl, 3-trifluoromethylphenyl, 5-fluoro-2-methoxyphenyl, 4-fluoro-2-methoxyphenyl, 2,3-dichlorophenyl or 2-(trifluoromethyl)pyridin-3-yl;

$R_2$ represents a hydrogen atom, a fluorine or chlorine atom, a trifluoromethyl radical, an —OCH₃ group, an —OCH₂CH₃ group, an —S—CH₃ group, an —S—CH₂—CH₃ group, an —SO—CH₂—CH₃ group, an —SO₂CH₃ group, an —SO₂CH₂CH₃ group, an —NHSO₂—CH₃ group, an —NHSO₂—CF₃ group, an —NHSO₂CHF₂ group, an —N(CH₃)—SO₂CH₃ group, an —NH—CO—CF₃ group, an —N(CH₃)—CO—CF₃ group, an —NH—SO₂—N(CH₃)₂ group or a —CO—N(CH₃)₂ group, which are placed on the terminal position of the alkyl chain;

$R_3$ represents a hydrogen atom, a chlorine atom, a methyl group, a methoxy group or a trifluoromethyl radical;

in the form of the base or of an addition salt with an acid.

Mention may in particular be made, among the compounds of formula (I) which are subject-matters of the invention, of the following compounds:

3-[3-Fluoro-2-(trifluoromethyl)phenyl]-8-methoxy-1-pentylcinnolin-4(1H)-one;
3-[2-Fluoro-3-(trifluoromethyl)phenyl]-8-methoxy-1-pentylcinnolin-4(1H)-one;
3-[2-Fluoro-3-(trifluoromethyl)phenyl]-1-pentylcinnolin-4(1H)-one;
3-[2-Fluoro-3-(trifluoromethyl)phenyl]-1-(5,5,5-trifluoropentyl)cinnolin-4(1H)-one;
8-Methoxy-1-pentyl-3-[3-(trifluoromethoxy)phenyl]cinnolin-4(1H)-one;
3-[2-Fluoro-3-(trifluoromethyl)phenyl]-1-(4,4,4-trifluorobutyl)cinnolin-4(1H)-one;
3-[2-Fluoro-3-(trifluoromethyl)phenyl]-1-[3-(methylthio)propyl]cinnolin-4(1H)-one;
1-(4-Fluorobutyl)-3-[2-fluoro-3-(trifluoromethyl)phenyl]cinnolin-4(1H)-one;
3-[2-Chloro-3-(trifluoromethyl)phenyl]-8-methoxy-1-pentylcinnolin-4(1H)-one;
3-[3-(Trifluoromethyl)phenyl]-1-(5,5,5-trifluoropentyl)cinnolin-4(1H)-one;
3-[2-Methoxy-5-fluorophenyl]1-(5,5,5-trifluoropentyl)cinnolin-4-(1H)-one;
1-Pentyl-3-[3-(trifluoromethyl)phenyl]cinnolin-4(1H)-one;
1-[3-(Methylthio)propyl]-3-[3-(trifluoromethyl)phenyl]cinnolin-4(1H)-one;
3-(4-Fluoro-2-methoxyphenyl)-1-(4,4,4-trifluorobutyl)cinnolin-4(1H)-one;
3-(5-Fluoro-2-methoxyphenyl)-1-(4,4,4-trifluorobutyl)cinnolin-4(1H)-one;
7 Chloro-3-[2-chloro-3-(trifluoromethyl)phenyl]-1-(5,5,5-trifluoropentyl)-cinnolin-4(1H)-one;
N-(3-[3-[2-Fluoro-3-(trifluoromethyl)phenyl]-8-methoxy-4-oxocinnolin-1(4H)-yl]propyl)methanesulphonamide;
N-[3-[3-[2-Chloro-3-(trifluoromethyl)phenyl]-8-methoxy-4-oxocinnolin-1(4H)-yl]propyl]methanesulphonamide;
N-[3-[3-[3-Fluoro-2-(trifluoromethyl)phenyl]-8-methoxy-4-oxocinnolin-1(4H)-yl]propyl]methanesulphonamide;
N-[3-[3-(2,3-Dichlorophenyl)-8-methoxy-4-oxocinnolin-1(4H)-yl]propyl]methanesulphonamide;
N-[3-[8-Methoxy-4-oxo-3-(trifluoromethyl)pyridin-3-yl]cinnolin-[(4H)-yl]propyl]methanesulphonamide;
N-[3-[3-(2,3-Dichlorophenyl)-4-oxo-7-(trifluoromethyl)cinnolin-1(4H)-yl]propyl]methanesulphonamide;
3-[2-Fluoro-3-(trifluoromethyl)phenyl]-1-(3-(methanesulphonyl)propyl)-8-methoxy-1H-cinnolin-4-one;
N-{3-[3-[2-Fluoro-3-(trifluoromethyl)phenyl]-4-oxo-7-trifluoromethyl-4H-cinnolin-1-yl]propyl}methanesulphonamide;
N-{3-[3-[3-Fluoro-2-(trifluoromethyl)phenyl]-4-oxo-7-trifluoromethyl-4H-cinnolin-1-yl]propyl}methanesulphonamide;
N-{3-[3-[2-Fluoro-3-(trifluoromethyl)phenyl]-4-oxo-4H-cinnolin-1-yl]-propyl}methanesulphonamide;
N-{3-[3-[2-Fluoro-3-(trifluoromethyl)phenyl]-7-methoxy-4-oxo-4H-cinnolin-1-yl]-propyl}methanesulphonamide;
1-[2-(Ethylthio)ethyl]-3-[2-fluoro-3-(trifluoromethyl)phenyl]-8-methoxycinnolin-4(1H)-one;
1-[2-(Ethylsulphinyl)ethyl]-3-[2-fluoro-3-(trifluoromethyl)phenyl]-8-methoxycinnolin-4(1H)-one;
1-[2-(Ethylsulphonyl)ethyl]-3-[2-fluoro-3-(trifluoromethyl)phenyl]-8-methoxycinnolin-4(1H)-one;
3-(2,3-Dichlorophenyl)-1-[2-(ethylthio)ethyl]-8-methoxycinnolin-4(1H)-one;
3-(2,3-Dichlorophenyl)-1-[2-(ethylsulphinyl)ethyl]-8-methoxycinnolin-4(1H)-one;
3-(2,3-Dichlorophenyl)-1-[2-(ethylsulphonyl)ethyl]-8-methoxycinnolin-4(1H)-one;
N-(3-{8-Methoxy-4-oxo-3-[3-(trifluoromethoxy)phenyl]cinnolin-1(4H)-yl}propyl)methanesulphonamide;
1,1,1-Trifluoro-N-(3-{3-[2-fluoro-3-(trifluoromethyl)phenyl]-8-methoxy-4-oxocinnolin-1(4H)-yl}propyl)methanesulphonamide;
2,2,2-Trifluoro-N-(3-{3-[2-fluoro-3-(trifluoromethyl)phenyl]-8-methoxy-4-oxocinnolin-1(4H)-yl}propyl)acetamide;

N-(3-{7-Chloro-3-[2-fluoro-3-(trifluoromethyl)phenyl]-4-oxocinnolin-1(4H)-yl}propyl)methanesulphonamide;
N-{3-[3-(2,3-Dichlorophenyl)-8-methoxy-4-oxocinnolin-1(4H)-yl]propyl}-N-methylmethanesulphonamide;
1-[2-(Ethylthio)ethyl]-3-[2-fluoro-3-(trifluoromethyl)phenyl]-8-(trifluoromethoxy)cinnolin-4(1H)-one;
7-Chloro-1-[2-(ethylthio)ethyl]-3-[2-fluoro-3-(trifluoromethyl)phenyl]cinnolin-4(1H)-one;
7-Chloro-1-[2-(ethylsulphonyl)ethyl]-3-[2-fluoro-3-(trifluoromethyl)phenyl]cinnolin-4(1H)-one;
7-Chloro-3-(2,3-dichlorophenyl)-1-[2-(ethylthio)ethyl]cinnolin-4(1H)-one;
2,2,2-Trifluoro-N-(3-{3-[2-fluoro-3-(trifluoromethyl)phenyl]-8-methoxy-4-oxocinnolin-1(4H)-yl}propyl)-N-methylacetamide;
N-(3-{7-Chloro-3-[3-fluoro-2-(trifluoromethyl)phenyl]-4-oxocinnolin-1(4H)-yl}propyl)methanesulphonamide;
7-Chloro-1-[2-(ethylthio)ethyl]-3-[3-(trifluoromethoxy)phenyl]cinnolin-4(1H)-one;
7-Chloro-3-(2,3-dichlorophenyl)-1-[2-(ethylsulphinyl)ethyl]cinnolin-4(1H)-one;
7-Chloro-3-(2,3-dichlorophenyl)-1-[2-(ethylsulphonyl)ethyl]cinnolin-4(1H)-one;
1-[2-(Ethylthio)ethyl]-8-methoxy-3-[3-(trifluoromethoxy)phenyl]cinnolin-4(1H)-one;
1-[2-(Ethylsulphonyl)ethyl]-8-methoxy-3-[3-(trifluoromethoxy)phenyl]cinnolin-4(1H)-one;
3-(2,3-Dichlorophenyl)-1-(2-ethoxyethyl)-8-methoxycinnolin-4(1H)-one;
1-(2-Ethoxyethy 1)-3-[2-fluoro-3-(trifluoromethyl)phenyl]-8-methoxycinnolin-4(1H)-one;
N'-{3-[3-(2,3-Dichlorophenyl)-8-methoxy-4-oxocinnolin-1(4H)-yl]propyl}-N,N-dimethylsulphamide;
1,1-Difluoro-N-(3-{3-[2-fluoro-3-(trifluoromethyl)phenyl]-8-methoxy-4-oxocinnolin-1(4H)-yl}propyl)methanesulphonamide;
N-(2-{3-[2-Fluoro-3-(trifluoromethyl)phenyl]-8-methoxy-4-oxocinnolin-1(4H)-yl}ethyl)methanesulphonamide;
3-{3-[2-Fluoro-3-(trifluoromethyl)phenyl]-8-methoxy-4-oxocinnolin-1(4H)-yl}-N,N-dimethylpropanamide;
3-[2-Fluoro-3-(trifluoromethyl)phenyl]-8-methoxy-1-(3-methoxy-3-methyl buty 1)cinnolin-4(1H)-one;
3-(2,3-Dichlorophenyl)-8-methoxy-1-(3-methoxy-3-methylbutyl)cinnolin-4(1H)-one;
3-[3-Fluoro-2-(trifluoromethyl)phenyl]-8-methoxy-1-(3-methoxy-3-methylbutyl)cinnolin-4(1H)-one;
8-Fluoro-3-[2-fluoro-3-(trifluoromethyl)phenyl]-1-(3-methoxy-3-methylbutyl)cinnolin-4(1H)-one;
in the form of the base or of an addition salt with an acid.

In that which follows, protective group PG is understood to mean a group which makes it possible, on the one hand, to protect a reactive functional group, such as a hydroxyl or an amine, during a synthesis and, on the other hand, to regenerate the reactive functional group intact at the end of the synthesis. Examples of protective groups and protection and deprotection methods are given in "Protective Groups in Organic Synthesis", Green et al., 4th Edition (John Wiley & Sons Inc., New York), 2007.

Leaving group is understood to mean, in that which follows, a group which can be easily cleaved from a molecule by splitting a heterolytic bond with departure of an electron pair. This group can thus easily be replaced by another group during a substitution reaction, for example. Such leaving groups are, for example, halogens or an activated hydroxyl group, such as a methanesulphonate, benzenesulphonate, p-toluenesulphonate, initiate, acetate, and the like. Examples of leaving groups and references for their preparation are given in "Advanced Organic Chemistry", M. B. Smith and J. March, 6th edition, Wiley Interscience, 2007, pp. 496-501.

In accordance with the invention, the compounds of formula (I) can be prepared according to a process which is characterized in that:
a compound of formula:

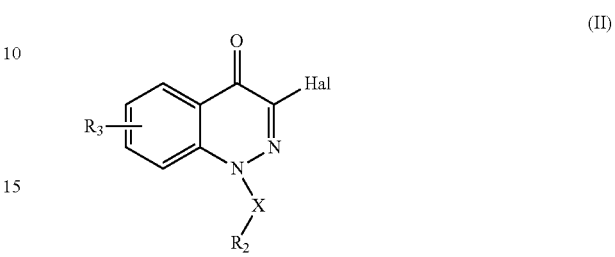

(II)

in which X, $R_2$ and $R_3$ are as defined for a compound of formula (I) and Hal represents a halogen atom, is reacted in the presence of a base with a compound of formula:

$R_1$—B(OH)$_2$ (III)

in which $R_1$ is as defined for a compound of formula (I).

The reaction can be carried out in the presence of a palladium catalyst, such as, for example, tetrakis(triphenylphosphine)palladium, in the presence of a base, such as, for example, sodium carbonate, in a solvent, such as, for example, toluene, methanol, ethanol or a mixture of these solvents, at a temperature of between ambient temperature and 100° C.

Optionally, the compound of formula (I) is converted to one of its addition salts with inorganic and/or organic acids.

The compounds of formula (I) thus obtained can subsequently be separated from the reaction medium and purified according to conventional methods, for example by crystallization or chromatography.

The compounds of formula (I) thus obtained are isolated in the free base or salt form, according to conventional techniques.

According to an alternative form of this process, a compound of formula (I) in which $R_2$ represents an —S-Alk group can also be prepared by reaction of a compound of formula:

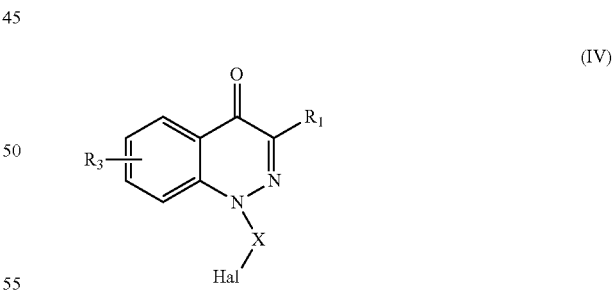

(IV)

in which X, $R_1$ and $R_3$ are as defined for a compound of formula (I) and Hal represents a halogen atom, with a sodium alkanethiolate derivative of formula:

NaS-Alk (V)

in which Alk is as defined for a compound of formula (I).

The reaction is carried out in a solvent, such as ethanol, at a temperature of between ambient temperature and the reflux temperature of the solvent.

According to another alternative form of the above processes, a compound of formula (I) in which $R_2$ represents —SOAlk or —SO$_2$Alk can be prepared by the reaction of a compound of formula (I) in which R$_2$ represents —SAlk with an oxidizing agent. Use may be made, as oxidizing agent, for example, of aqueous hydrogen peroxide solution or 3-chloroperbenzoic acid, in a solvent, such as dichloromethane, at a temperature of between 0° C. and ambient temperature.

According to the number of equivalents of oxidizing agent used and according to the temperature of the reaction, a sulphoxide (R$_2$=—SOAlk) or sulphone (R$_2$=—SO$_2$Alk) is obtained. It is also possible to obtain a mixture of the two compounds, which is separated using processes known to a person skilled in the art, for example by preparative chromatography.

The compounds of formula (II) are prepared by reaction of a compound of formula:

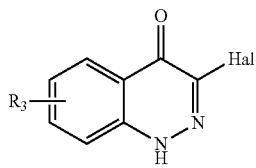

(VI)

in which R$_3$ is as defined for a compound of formula (I) and Hal represents a halogen atom, with a compound of formula:

Y—X—R$_2$  (VII)

in which X and R$_2$ are as defined for a compound of formula (I) and Y represents a halogen atom or a hydroxyl.

When Y=Hal, the reaction is carried out in the presence of a strong base, such as, for example, sodium hydride, in a solvent, such as, for example, N,N-dimethylformamide, at a temperature of between 0° C. and the reflux temperature of the solvent.

When Y=OH, the reaction is carried out in the presence of diethyl azodicarboxylate and triphenylphosphine in a solvent, such as, for example, tetrahydrofuran, and at a temperature between 0° C. and ambient temperature.

According to an alternative form of this process, the compounds of formula (II) in which R$_2$=—N(R$_4$)—SO$_2$Alk with R$_4$=H can also be prepared by reaction of a compound of formula:

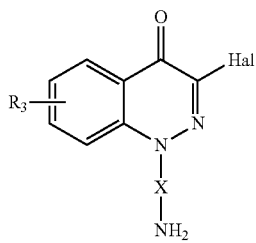

(XIX)

in which X and R$_3$ are as defined for a compound of formula (I) and Hal represents a halogen atom, with a compound of formula:

Hal-SO$_2$Alk  (XX)

in which Alk is as defined for a compound of formula (I) and Hal represents a halogen atom.

The reaction is carried out in the presence of a base, such as, for example, triethylamine, in a solvent, such as, for example, dichloromethane, at a temperature of between 0° C. and ambient temperature.

The compounds of formula (II) in which R$_2$=—N(R$_4$)SO$_2$Alk with R$_4$ other than H can be prepared by reaction of the compounds of formula (II) in which R$_2$=—NHSO$_2$Alk with an alkylating agent, in the presence of a base. Use is made, as alkylating agent, for example, of a dialkyl sulphate of formula SO$_4$(R$_4$)$_2$ or an alkyl halide of formula R$_4$Hal, in which formulae R$_4$=(C$_1$-C$_4$)alkyl and Hal represents a halogen atom, in the presence of a strong base, such as, for example, sodium hydride, for example.

The compounds of formula (II) in which R$_2$=—N(R$_4$)SO$_2$—N(Alk)$_2$ can be prepared according to the same procedures described above for R$_2$=N(R$_4$)SO$_2$Alk starting from a compound of formula (XIX) and a compound of formula Hal-SO$_2$—N(Alk)$_2$ (XXa).

The compounds of formula (III) are commercially available, known or prepared according to methods known to a person skilled in the art.

The compounds of formula (IV) are prepared by reaction of a compound of formula:

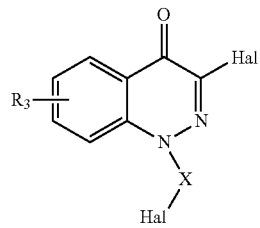

(VIII)

in which X and R$_3$ are as defined for a compound of formula (I) and Hal represents a halogen atom, with a compound of formula (III).

The reaction is carried out in the presence of a palladium catalyst, such as, for example, tetrakis(triphenylphosphine) palladium, in the presence of a base, such as, for example, sodium carbonate, in a solvent, such as, for example, toluene, methanol, ethanol or a mixture of these solvents, at a temperature of between ambient temperature and 100° C.

The compounds of formula (V) are commercially available, known or prepared according to methods known to the person skilled in the art.

The compounds of formula (VI) in which Hal represents a bromine atom are prepared from a compound of formula:

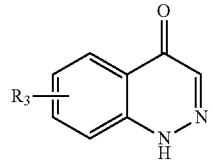

(IX)

in which R$_3$ is as defined for a compound of formula (I), by reaction with bromine in the presence of a base, such as, for example, potassium ethoxide, in a solvent, such as, for example, acetic acid, at a temperature of between ambient temperature and the reflux temperature of the solvent.

The compounds of formula (VI) in which Hal represents an iodine atom are prepared by reaction of a compound of formula (IX) with iodine in the presence of phenyl[bis(2,2,2-trifluoroacetoxy)]-λ³-iodane and a base, such as, for example, pyridine, in a solvent, such as, for example, dichloromethane, at ambient temperature.

The compounds of formula (VII) are commercially available, known or prepared according to methods known to a person skilled in the art.

The compounds of formula (VIII) are prepared by reaction of a compound of formula (VI) in which $R_3$ is as defined for a compound of formula (I) with a compound of formula:

Hal-X-Hal (X)

in which Hal represents a halogen atom and X is as defined for a compound of formula (I). The reaction is carried out in the presence of a strong base, such as, for example, sodium hydride, in a solvent, such as, for example, N,N-dimethylformamide, at a temperature of between 0° C. and the reflux temperature of the solvent.

The compounds of formula (IX) are prepared by cyclization of a compound of formula:

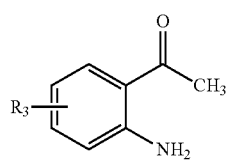

(XI)

in which $R_3$ is as defined for a compound of formula (I), in the presence of sodium nitrite, in a solvent, such as, for example, hydrochloric acid, at a temperature of between 0° C. and ambient temperature.

The compounds of formula (X) are commercially available, known or prepared according to methods known to a person skilled in the art.

The compounds of formula (XI) in which $R_3$ is as defined for a compound of formula (I) are prepared according to Scheme I below.

SCHEME I

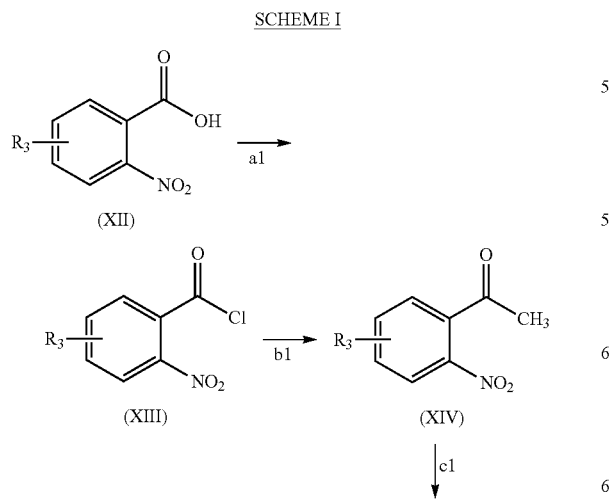

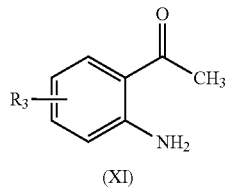

(XI)

In stage a1 of Scheme I, the reaction of a compound of formula (XII) with sulphonyl chloride is carried out at a temperature of between ambient temperature and 100° C.

In stage b1, the compound of formula (XIII) thus obtained is reacted with diethyl malonate in the presence of magnesium in a solvent, such as, for example, an ether (for example diethyl ether), at a temperature of between ambient temperature and the reflux temperature of the solvent.

The compound (XIV) thus obtained is reduced in stage c1 in the presence of zinc and acetic acid in a solvent, such as, for example, tetrahydrofuran, and at a temperature of between 0° C. and ambient temperature.

The compound of formula (XII) is commercially available, known or prepared according to methods known to a person skilled in the art.

According to an alternative form of this process, it is also possible to prepare a compound of formula (XI) in which $R_3$ is as defined for a compound of formula (I) according to Scheme II.

SCHEME II

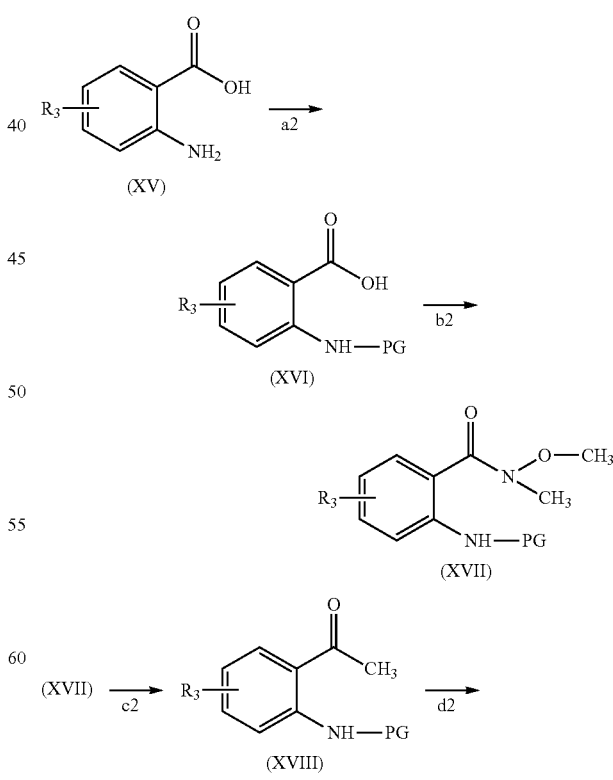

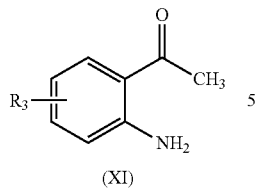

(XI)

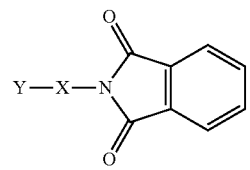

(XXII)

In stage a2 of Scheme II, the amine of the compound of formula (XV) is protected according to methods known to a person skilled in the art.

In stage b2, the compound of formula (XVI) thus obtained is reacted with N-methoxymethanamine in the presence of a coupling agent used in peptide chemistry, such as, for example, 1,3-dicyclohexylcarbodiimide (DCC) or (benzotriazol-1-yloxy)tris(dimethylamino)phosphonium hexafluorophosphate (BOP) or (benzotriazol-1-yloxy)tripyrrolidinophosphonium hexafluorophosphate (PyBOP) or 2-(1H-benzotriazol-1-yl)-1,1,3,3-tetramethyluronium tetrafluoroborate, in the presence of a base, such as, for example, triethylamine, N,N-diisopropylethylamine or 4-dimethylaminopyridine, in a solvent, such as, for example, dichloromethane, dichloroethane, N—N-dimethylformamide or tetrahydrofuran, at a temperature of between −10° C. and the reflux temperature of the solvent.

The compound (XVII) thus obtained is reacted in stage c2 with an organometallic compound, such as methylmagnesium bromide, in a solvent, such as an ether (for example tetrahydrofuran or dioxane), at a temperature of between −100° C. and ambient temperature.

The compound (XVIII) thus obtained is deprotected in stage d2.

The compounds (XIX) are prepared by reaction of a compound of formula:

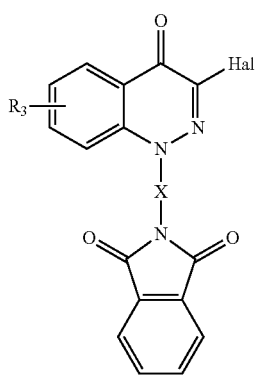

(XXI)

in which X and $R_3$ are as defined for a compound of formula (I) and Hal represents a halogen atom, with hydrazine monohydrate in a solvent, such as, for example, methanol, at a temperature of between ambient temperature and the reflux temperature of the solvent.

The compounds of formulae (XX) and (XXa) are commercially available, known or prepared according to methods known to a person skilled in the art.

The compounds of formula (XXI) are prepared by reaction of a compound of formula (VI), in which $R_3$ is as defined for a compound of formula (I), with a compound of formula:

in which X is as defined for a compound of formula (I) and Y represents a halogen atom or a hydroxyl.

Use may be made, as an alternative to the compound (XXII), of a compound of formula Hal-X—NHBOC with the compound of formula (VI).

When Y=Hal, the reaction is carried out in the presence of a strong base, such as, for example, sodium hydride, in a solvent, such as, for example, N,N-dimethylformamide, at a temperature of between 0° C. and the reflux temperature of the solvent.

When Y=OH, the reaction is carried out in the presence of diethyl azodicarboxylate and triphenylphosphine in a solvent, such as, for example, tetrahydrofuran, at a temperature of between 0° C. and ambient temperature.

The compounds of formula (XXII) are commercially available, known or prepared according to methods known to a person skilled in the art.

The following Examples describe the preparation of some compounds in accordance with the invention. These examples are not limiting and serve only to illustrate the present invention. The numbers of the compounds in the examples refer to those given in Table below, in which the chemical structures and the physical properties of a few compounds according to the invention are illustrated.

The following abbreviations are used in the Preparations and in the Examples:

| | |
|---|---|
| AcOEt: | ethyl acetate, |
| AcONa: | sodium acetate, |
| BOC: | tert-butyloxycarbonyl, |
| HPLC: | high performance liquid chromatography, |
| DCM: | dichloromethane, |
| DIPEA: | diisopropylethylamine, |
| DMF: | N,N-dimethylformamide, |
| DMSO: | dimethyl sulphoxide, |
| ether: | diethyl ether, |
| iso ether: | diisopropyl ether, |
| M.p.: | melting point, |
| HBr: | hydrobromic acid |
| MeOH: | methanol, |
| AT: | ambient temperature, |
| Tetrakis: | tetrakis(triphenylphosphine)palladium, |
| TFA: | trifluoroacetic acid, |
| THF: | tetrahydrofuran. |

The proton nuclear magnetic resonance ($^1$H NMR) spectra are recorded at 200 MHz in $d_6$-DMSO. The chemical shifts δ are expressed in parts per million (ppm). Use is made of the following abbreviations in interpreting the spectra: s: singlet, d: doublet, t: triplet, q: quartet, m: unresolved peak, mt: multiplet, bs: broad singlet, sd: split doublet.

The mixtures of solvents are quantified as ratios by volume.

The compounds according to the invention are analysed by coupled LC/UV/MS (Liquid Chromatography/UV detection/Mass spectrometry). The molecular peak (MH$^+$) and the retention time (rt) in minutes are measured.

The conditions used are as follows:
Conditions A
Column: Symmetry $C_{18}$ (2.1×50 mm) 3.5 μm;
Eluent: A: $H_2O$+0.005% TFA pH≈3;
B: acetonitrile/0.005% TFA;
Gradient:

| Time (min) | % A | % B |
| --- | --- | --- |
| 0 | 100 | 0 |
| 10 | 10 | 90 |
| 15 | 10 | 90 |
| 16 | 0 | 100 |
| 20 | 0 | 100 |

Flow rate: 0.4 ml/minute;
UV detection: λ=210-220 nm.
Conditions B
An XTerra MS $C_{18}$ (2.1×50 mm) 3.5 μm column is used;
Eluent: A: 10 mM $AcONH_4$ pH≈7;
B: acetonitrile;
Gradient:

| Time (min) | % A | % B |
| --- | --- | --- |
| 0 | 100 | 0 |
| 10 | 10 | 90 |
| 15 | 10 | 90 |
| 16 | 100 | 0 |
| 20 | 100 | 0 |

Flow rate: 0.4 ml/minute;
UV detection: λ=220 nm.
Conditions C
An Acquity BEH $C_{18}$ (2.1×50 mm) 1.7 μm column is used;
Eluent: A: $H_2O$+0.05% TFA pH≈3; acetonitrile (97/3)
B: acetonitrile/0.035% TFA;
Gradient:

| Time (min) | % A | % B |
| --- | --- | --- |
| 0 | 100 | 0 |
| 2.3 | 5 | 95 |
| 2.9 | 5 | 95 |
| 3 | 100 | 0 |
| 3.5 | 100 | 0 |

Flow rate: 1 ml/minute;
UV detection: λ=220 nm.
The mass spectra are recorded in positive electrospray (ESI) mode in order to observe the ions resulting from the protonation of the compounds analysed ($MH^+$) or from the formation of adducts with other cations, such as $Na^+$, $K^+$, and the like.

Preparations

1. Preparations of the Compounds of Formula (XI)

Preparation 1.1

1-(2-Amino-3-methoxyphenyl)ethanone (XI): $R_3$=3-OMe

A—3-Methoxy-2-nitrobenzoyl chloride

A mixture of 10 g of 3-methoxy-2-nitrobenzoic acid in 60 ml of thionyl chloride is heated at 75° C. for 3 hours. The reaction mixture is concentrated under vacuum and 10.9 g of the expected compound are obtained, which product is used as is in the following stage.

B—1-(3-Methoxy-2-nitrophenyl)ethanone

A solution of 20 ml of diethyl malonate in 12 ml of EtOH is added, dropwise and at AT, to a mixture of 3.2 g of magnesium in 10 ml of ether, then a solution of 10.9 g of the compound from the preceding stage in 40 ml of ether is added dropwise and the mixture is heated at reflux for 18 hours. The reaction mixture is run into 50 ml of ether and insoluble material is filtered off. The insoluble material is taken up in a saturated $NH_4Cl$ solution, extraction is carried out with 100 ml of chloroform, the aqueous phase is acidified by addition of 20 ml of a 10% HCl solution, the aqueous phase is reextracted with 100 ml of chloroform, the combined organic phases are dried over $MgSO_4$ and the solvents are evaporated under vacuum. The residue is taken up in a mixture of 10 ml of acetic acid, 1.5 ml of $H_2SO_4$ and 7 ml of water and then heated at reflux for 5 hours. The acetic acid is concentrated under vacuum, the reaction mixture is taken up in 100 ml of water, the aqueous phase is basified by addition of $NH_4OH$, extraction is carried out with 100 ml of chloroform, the organic phase is washed with a saturated NaCl solution and dried over $MgSO_4$, and the solvent is evaporated under vacuum. The residue is chromatographed on silica gel, elution being carried out with the gradient of the cyclohexane/AcOEt mixture from 80/20 (v/v) to 20/80 (v/v). 3.3 g of the expected compound are obtained.

C—1-(2-Amino-3-methoxyphenyl)ethanone

A solution of 3.3 g of the compound from the preceding stage in 100 ml of THF is cooled to 0° C., 13.27 g of zinc and 15.7 ml of acetic acid are added, the mixture is then left stirring while allowing the temperature to rise to AT and is left stirring at AT for 4 hours. The reaction mixture is filtered through Célite® and the filtrate is concentrated under vacuum. The residue is extracted with THF, the organic phase is washed with 100 ml of a 10% NaOH solution and with a saturated NaCl solution and dried over $MgSO_4$, and the solvent is evaporated under vacuum. The residue is chromatographed on silica gel, elution being carried out with the gradient of the cyclohexane/AcOEt mixture from 80/20 (v/v) to 60/40 (v/v). 2 g of the expected compound are obtained.

Preparation 1.2

1-(2-Amino-4-chlorophenyl)ethanone (XI): $R_3$=4-Cl

A—2-[(tert-Butoxycarbonyl)amino]-4-chlorobenzoic acid 19.5 ml of triethylamine are added to a mixture of 10 g of 2-amino-4-chlorobenzoic acid in 45 ml of dioxane and 15 ml of water, a solution of 14.73 g of di(tert-butyl) dicarbonate in 30 ml of dioxane is then added dropwise and the mixture is left stirring at AT for 48 hours. The reaction mixture is concentrated under vacuum, the residue is taken up in 100 ml of a water/AcOEt mixture, the layers are separated by settling, the organic phase is washed with a saturated NaCl solution and dried over $MgSO_4$, and the solvent is evaporated under vacuum. The residue is chromatographed on silica gel, elution being carried out with the gradient of the cyclohexane/AcOEt mixture from 80/20 (v/v) to 50/50 (v/v). 5.35 g of the expected compound are obtained.

B—tert-Butyl[5-chloro-2-[methoxy(methyl)carbamoyl]phenyl]carbamate 8.78 ml of triethylamine and then 2.11 g of N-methoxymethanamine and 11.27 g of PyBOP are added to a solution of 5.35 g of the compound from the preceding stage in 200 ml of DCM and the mixture is left stirring at AT overnight. The reaction mixture is washed with water, with a 10% NaOH solution and with a saturated NaCl solution and dried over MgSO$_4$, and the solvent is evaporated under vacuum. The residue is chromatographed on silica gel, elution being carried out with the gradient of the cyclohexane/AcOEt mixture from 80/20 (v/v) to 60/40 (v/v). 5.7 g of the expected compound are obtained.

C—tert-Butyl (2-acetyl-5-chlorophenyl)carbamate

A solution of 5.7 g of the compound from the preceding stage in 445 ml of THF is cooled to −40° C., 38.8 ml of methylmagnesium bromide are added dropwise and the mixture is left stirring at AT overnight. The reaction mixture is run onto a 10% HCl solution, extraction is carried out with AcOEt, the organic phase is washed with a saturated NaCl solution and dried over MgSO$_4$, and the solvent is evaporated under vacuum. The residue is chromatographed on silica gel, elution being carried out with the cyclohexane/AcOEt mixture (80/20; v/v) and then up to 100% of AcOEt. 2.05 g of the expected compound are obtained.

D—1-(2-Amino-4-chlorophenyl)ethanone 2.55 ml of trifluoroacetic acid are added dropwise to a solution of 0.9 g of the compound from the preceding stage in 17 ml of DCM and the mixture is left stirring at AT overnight. The reaction mixture is washed with a 10% NaOH solution and with a saturated NaCl solution and dried over MgSO$_4$, and the solvent is evaporated. 0.6 g of the expected compound is obtained.

2. Preparations of the Compounds of Formula (IX)

Preparation 2.1

8-Methoxycinnolin-4(1H)-one (IX): R$_3$=8-OMe

A solution of 2 g of the compound from Preparation 1.1 in 8 ml of concentrated HCl is cooled to 0° C., a solution of 1.25 g of NaNO$_2$ in 2.7 ml of water is added dropwise while maintaining the temperature of the reaction mixture below 10° C. and the mixture is left stirring at 0° C. for 2 hours and at overnight. The reaction mixture is concentrated under vacuum, 50 ml of an AcONa solution are added and the precipitate formed is filtered off and washed with 20 ml of water. 1.95 g of the expected compound are obtained.

Preparation 2.2

7-Chlorocinnolin-4(1H)-one (IX): R$_3$=7-Cl

A solution of 1.8 g of the compound from Preparation 1.2 in 7 ml of concentrated HCl is cooled to 0° C., a solution of 1.1 g of NaNO$_2$ in 2.39 ml of water is added dropwise while maintaining the temperature of the reaction mixture below 10° C. and the mixture is left stirring at 0° C. for 2 hours and at AT overnight. The reaction mixture is concentrated under vacuum, 50 ml of an AcONa solution are added and the precipitate formed is filtered off and washed with 20 ml of water. 1.6 g of the expected compound are obtained.

3. Preparations of the Compounds of Formula (VI)

Preparation 3.1

3-Bromo-8-methoxycinnolin-4(1H)-one (VI): R$_3$=8-OMe; Hal=Br 1.4 g of EtOK are added to a mixture of 1.95 g of the compound from Preparation 2.1 in 20 ml of AcOH and the combined mixture is heated to reflux. A solution of 0.68 ml of bromine in 2 ml of AcOH is subsequently added dropwise and the mixture is heated at reflux for 1 hour 30 minutes. The AcOH is concentrated under vacuum, the residue is taken up in water and the precipitate formed is filtered off, washed with water and dried. 2.8 g of the expected compound are obtained.

Preparation 3.2

3-Bromo-7-chlorocinnolin-4(1H)-one (VI): R$_3$=7—Cl; Hal=Br 1.26 g of EtOK are added to a mixture of 1.8 g of the compound from Preparation 2.2 in 15 ml of AcOH and the combined mixture is heated to reflux. A solution of 0.77 ml of bromine in 5 ml of AcOH is subsequently added dropwise and the mixture is heated at reflux for 3 hours. The AcOH is concentrated under vacuum, the residue is taken up in water and the precipitate formed is filtered off, washed with water and dried. 2.4 g of the expected compound are obtained.

Preparation 3.3

3-Bromocinnolin-4(1H)-one (VI): R$_3$=H; Hal=Br

Compound prepared according to the procedure described in Preparation 3.1.

Preparation 3.4

3-Iodo-8-methoxycinnolin-4(1H)-one (VI): R$_3$=8-OMe; Hal=I 8.2 g of iodine and 5.19 ml of pyridine are added to a mixture of 9.5 g of the compound from Preparation 2.1 and 13.91 g of phenyl[bis(2,2,2-trifluoroacetoxy)]-$\lambda^3$-iodane in 270 ml of DCM. The mixture is left stirring overnight at AT. The precipitate formed is filtered off, washed with n-pentane and then dried. 13.2 g of the expected compound are obtained.

4. Preparations of the Compounds of Formula (II)

Preparation 4.1

3-Bromo-8-methoxy-1-pentylcinnolin-4(1H)-one (II): X=—(CH$_2$)$_5$—; R$_2$=H; R$_3$=8OMe; Hal=Br A suspension of 0.33 g of NaH, at 60% in oil, in 15 ml of DMF is cooled to 0-5° C., a solution of 1.4 g of the compound from Preparation 3.1 in 15 ml of DMF and then a solution of 1.08 ml of 1-iodopentane in 10 ml of DMF are added dropwise and the mixture is heated at 75° C. for 3 hours. The reaction mixture is poured into water and extracted with DCM, the organic phase is washed with a saturated NaCl solution and dried over $MgSO_4$, and the solvent is evaporated in a vacuum. The residue is chromatographed on silica gel, elution being carried out with the gradient of the cyclohexane/AcOEt mixture from 80/20 (v/v) to 50/50 (v/v). 0.65 g of the expected compound is obtained.

Preparation 4.2

3-Bromo-7-chloro-1-(5,5,5-trifluoropentyl)cinnolin-4(1H)-one (II): $X=\text{—}(CH_2)_4\text{—}$; $R_2=CF_3$; $R_3=7\text{-Cl}$; Hal=Br A suspension of 0.55 g of NaH, at 60% in oil, in 20 ml of DMF is cooled to 0 to 5° C., a solution of 2.4 g of the compound from Preparation 3.2 in 30 ml of DMF is added dropwise, a solution of 2.8 g of 5-bromo-1,1,1-trifluoropentane in 10 ml of DMF is then added dropwise and the mixture is heated at 75° C. for 3 hours. The reaction mixture is run into water and extracted at the DCM, the organic phase is washed with a saturated NaCl solution and dried over $MgSO_4$, and the solvent is evaporated under vacuum. The residue is chromatographed on silica gel, elution being carried out with the gradient of the cyclohexane/AcOEt mixture from 80/20 (v/v) to 40/60 (v/v). 1.4 g of the expected compound are obtained.

Preparation 4.3

N-[3-(3-Bromo-8-methoxy-4-oxocinnolin-1(4H)-yl)propyl]methanesulphonamide (II): $X=\text{—}(CH_2)_3\text{—}$; $R_2=\text{—}NHSO_2Me$; $R_3=8\text{-OMe}$; Hal=Br A—2-[3-(3-Bromo-8-methoxy-4-oxocinnolin-1(4H)-yl)propyl]-1H-isoindole-1,3(2H)-dione (XXI)

A suspension of 0.77 g of NaH, at 60% in oil, in 15 ml of DMF is cooled to 0-5° C., a solution of 3.3 g of a compound from Preparation 3.1 in 50 ml of DMF is added dropwise, then a solution of 5.2 g of 2-(3-bromopropyl)-1H-isoindole-1,3(2H)-dione in 20 ml of DMF is added dropwise and the mixture is heated at 75° C. for 6 hours and left to return to AT overnight.

The reaction mixture is run into water and extracted with DCM, the organic phase is washed with a saturated NaCl solution and dried over $MgSO_4$, and the solvent is evaporated under vacuum. The residue is chromatographed on silica gel, elution being carried out with a gradient of the cyclohexane/AcOEt mixture from 90/10 (v/v) to 40/60 (v/v). 5 g of the expected compound are obtained.

B—1-(3-Aminopropyl)-3-bromo-8-methoxycinnolin-4(1H)-one (XIX)

0.66 ml of hydrazine monohydrate is added to a solution of 3 g of the compound from the preceding stage in 20 ml of MeOH and the mixture is heated at reflux for 4 hours. The reaction mixture is concentrated under vacuum, the residue is taken up in a 10% NaOH solution and extracted with DCM, the organic phase is washed with a saturated NaCl solution and dried over $MgSO_4$, and the solvent is evaporated under vacuum. 1.87 g of the expected compound are obtained.

C—N-[3-(3-Bromo-8-methoxy-4-oxocinnolin-1(4H)-yl)propyl]-methanesulphonamide

A mixture of 1.87 g of the compound from the preceding stage, 1.84 ml of triethylamine and 0.51 ml of methanesulphonyl chloride in 75 ml of DCM is left stirring overnight at AT. The reaction mixture is washed with a 10% HCl solution and with a 10% NaOH solution, and the precipitate formed is filtered off and dried. 2 g of the expected compound are obtained.

Preparation 4.4

1,1,1-Trifluoro-N-[3-(3-iodo-8-methoxy-4-oxocinnolin-1(4H)-yl)propyl]methanesulphonamide (II): $X=\text{—}(CH_2)_3\text{—}$; $R_2=\text{—}NHSO_2CF_3$; $R_3=8\text{-OMe}$; Hal=I A suspension of 0.3 g of NaH, at 60% in oil, in 5 ml of DMF is cooled to 5° C., a solution of 0.75 g of the compound from preparation 3.4 in 10 ml of DMF is added dropwise, a solution of 2 g of a compound from Preparation 7 in 10 ml of DMF is then added dropwise and the mixture is left stirring while allowing the temperature to rise to AT. The reaction mixture is heated at 100° C. for 48 hours. It is run into water and extracted with DCM, the organic phase is washed with a saturated NaCl solution and dried over $MgSO_4$, and the solvent is evaporated under vacuum. The residue is chromatographed on silica gel, elution being carried out with the gradient of the cyclohexane/AcOEt mixture from 80/20 (v/v) to 50/50 (v/v). The expected compound is obtained.

Preparation 4.5

8-Fluoro-3-iodo-1-(3-methoxy-3-methylbutyl)cinnolin-4(1H)-one (II): $X=CH_2CH_2C(CH_3)_2\text{—}$; $R_2=\text{—}OCH_3$; $R_3=8\text{-F}$; Hal=I A mixture of 0.72 g of 8-fluoro-3-iodocinnolin-4(1H)-one and 0.48 ml of 3-methoxy-3-methylbutan-1-ol in 20 ml of THF is cooled to 5° C., 0.97 g of triphenylphosphine is added and then 0.65 g of diethyl azodicarboxylate is slowly added, and the mixture is left stirring overnight at AT. The reaction mixture is concentrated under vacuum and the residue is chromatographed on silica gel, elution being carried out with the cyclohexane/AcOEt mixture (75/25; v/v) and then with AcOEt. The expected compound is obtained.

Preparation 4.6

N-[2-(3-Iodo-8-methoxy-4-oxocinnolin-1(4H)-yl)ethyl]methanesulphonamide (II): $X=\text{—}(CH_2)_2\text{—}$; $R_2=\text{—}NHSO_2Me$; $R_3=8\text{—}OMe$; Hal=I A—2-[2-(3-Iodo-8-methoxy-4-oxocinnolin-1(4H)-yl)ethyl]-1H-isoindole-1,3(2H)-dione (XXI)

A mixture of 2 g of the compound from Preparation 3.4 and 2.5 g of 2-(2-hydroxyethyl)-1H-isoindole-1,3(2H)-dione in 50 ml of THF is cooled to 5° C., 3.47 g of triphenylphosphine are added and then 2.3 g of diethyl azodicarboxylate are slowly added. After stirring at AT for 45 minutes, the reaction mixture is concentrated under vacuum, the residue is taken up in DCM and the precipitate formed is filtered off. 3.15 g of the expected compound are obtained.

B—1-(2-aminoethyl)-3-iodo-8-methoxycinnolin-4(1H)-one hydrochloride (XIX)

0.31 ml of hydrazine monohydrate is added to a solution of 1.5 g of the compound from the preceding stage in 12 ml of MeOH and the mixture is heated at 65° C. for 3 hours. The reaction mixture is concentrated under vacuum, the residue is taken up in a 10% NaOH solution and extracted with DCM, the organic phase is washed with a saturated NaCl solution and dried over MgSO$_4$, and the solvent is evaporated under vacuum. The product thus obtained is dissolved in a DCM/MeOH mixture, 2N ethereal hydrochloric acid is added and the precipitate formed is filtered off 0.88 g of the expected compound is obtained.

C—N-[2-(3-Iodo-8-methoxy-4-oxocinnolin-1(4H)-yl)ethyl]methanesulphonamide

A mixture of 0.4 g of the compound from the preceding stage, 0.58 ml of triethylamine and 0.09 ml of methanesulphonyl chloride in 20 ml of DCM is left stirring at AT for 48 hours. The reaction mixture is diluted by addition of a DCM/water mixture and the precipitate formed is filtered off. 0.21 g of the expected compound is obtained.

5. Preparations of the Compounds of Formula (VIII)

3-Bromo-1-(3-chloropropyl)cinnolin-4(1H)-one (VIII): X=—(CH$_2$)$_3$—; R$_3$=H; Hal=Cl
A suspension of 1.06 g of NaH, at 60% in oil, in 80 ml of DMF is cooled to 5° C., a solution of 4 g of the compound from Preparation 3.3 in 50 ml of DMF is added dropwise, a solution of 2.64 ml of 1-bromo-3-chloropropane in 50 ml of DMF is then added dropwise and the mixture is left stirring overnight while allowing the temperature to rise to AT. The reaction mixture is run into water and extracted with DCM, the organic phase is washed with a saturated NaCl solution and dried over MgSO$_4$, and the solvent is evaporated under vacuum. 4.9 g of the expected compound are obtained.

6. Preparations of the Compounds of Formula (IV)

1-(3-Chloropropyl)-3-[2-fluoro-(3-trifluoromethyl)phenyl]cinnolin-4(1H)-one (IV): X=—(CH$_2$)$_3$—;

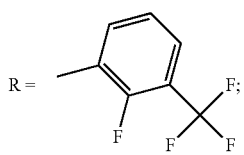

R$_3$=H; Hal=Cl
1.16 g of 2-fluoro-3-(trifluoromethyl)phenylboronic acid are subsequently added to a mixture of 1.4 g of the compound from Preparation 5 in 90 ml of a toluene/MeOH mixture (70/30; v/v), followed by 7.66 ml of a 2M Na$_2$CO$_3$ solution. Nitrogen is sparged into the reaction mixture for 30 minutes, 1.07 g of Tetrakis are subsequently added and the mixture is added at reflux for 1 hour 30 minutes. The reaction mixture is filtered through Celite® and then the filtrate is concentrated under vacuum. The residue is extracted with DCM, the organic phase is washed with a 10% NaOH solution and with a saturated NaCl solution and dried over MgSO$_4$, and the solvent is evaporated under vacuum. The residue is chromatographed on silica gel, elution being carried out with the cyclohexane/AcOEt mixture (70/30; v/v) up to 100% of AcOEt. 3.3 g of expected compound are obtained.

7. Preparations of the Compounds of Formula (VII)

N-(3-Bromopropyl)-1,1,1-trifluoromethanesulphonamide (VII): X=—(CH$_2$)$_3$—; Y=Br; R$_2$=—NHSO$_2$CF$_3$
5.1 ml of triethylamine and then 1.06 ml of trifluoromethanesulphonyl chloride are added, under a nitrogen atmosphere, to a solution of 2 g of 3-bromopropan-1-amine in 180 ml of DCM and the mixture is left stirring overnight at AT. The reaction mixture is washed with a buffer solution, pH=2, and with a saturated NaCl solution, the organic phase is dried over MgSO$_4$ and the solvent is evaporated under vacuum. 0.48 g of the expected compound is obtained in the form of an oil.

EXAMPLE 1

Compound No. 2

3-[2-Fluoro-3-(trifluoromethyl)phenyl]-8-methoxy-1-pentylcinnolin-4(1H)-one 0.11 g of [2-fluoro-3-(trifluoromethyl)phenyl]boronic acid is subsequently added to a solution of 0.15 g of the compound from Preparation 4.1 in 10 ml of a toluene/MeOH mixture (70/30; v/v), followed by 0.76 ml of a 2M Na$_2$CO$_3$ solution. Nitrogen is sparged into the reaction mixture for 20 minutes, 0.11 g of Tetrakis is added and the mixture is heated at 80° C. for 18 hours. The reaction mixture is filtered through Celite® and washing is carried out with AcOEt. The filtrate is washed with 30 ml of 10% NaOH and with a saturated NaCl solution and dried over MgSO$_4$, and the solvents are evaporated under vacuum. The residue is chromatographed on silica gel, elution being carried out with the gradient of the cyclohexane/AcOEt mixture from 90/10 (v/v) to 70/30 (v/v). 0.11 g of the expected compound is obtained, M.p.=82-84° C.
$^1$H NMR: d$_6$-DMSO (250 MHz): δ (ppm): 0.84: t: 3H; 1.22-1.42: m: 4H, 1.69-1.95 m: 2H; 4.03: s: 3H; 4.61-4.86: m: 2H; 7.42-7.61: m: 3H; 7.74-8.00: m: 3H.

EXAMPLE 2

Compound No. 17

7 Chloro-3-[2-chloro-3-(trifluoromethyl)phenyl]-1-(5,5,5-trifluoropentyl)-cinnolin-4(1H)-one 0.16 g of [2-chloro-3-(trifluoromethyl)phenyl]boronic acid is added to a solution of 0.25 g of the compound from Preparation 4.2 in 13 ml of a toluene/MeOH mixture (70/30; v/v), followed by 1.08 ml of a 2M Na$_2$CO$_3$ solution. Nitrogen is sparged into the reaction mixture for 20 minutes, 0.15 g of Tetrakis is added and the mixture is heated at 80° C. for 18 hours. The reaction mixture is filtered through Celite® and washing is carried out with AcOEt. The filtrate is washed with 30 ml of 10% NaOH and with a saturated NaCl solution and dried over MgSO$_4$, and the solvents are evaporated under vacuum. The residue is chromatographed on silica gel, elution being carried out with the gradient of the cyclohexane/AcOEt mixture from 90/10 (v/v) to 70/30 (v/v). 0.19 g of the expected compound is obtained, M.p.=137-138° C.

$^1$H NMR: $d_6$-DMSO (250 MHz): δ (ppm): 1.46-1.71: m: 2H; 1.78-2.01: m: 2H; 2.16-2.42: m: 2H; 4.57: t: 2H; 7.55-7.64: m, 1H; 7.69: t: 1H; 7.77-7.85: m: 1H; 7.94-8.04: m: 1H; 8.17-8.26: m: 2H.

EXAMPLE 3

Compound No. 7

3-(2-Fluoro-3-(trifluoromethyl)phenyl)-1-[3-(methylthio)propyl]cinnolin-4(1H)-one A mixture of 0.33 g of the compound from Preparation 6 and 0.12 g of sodium methanethiolate in 5 ml of ethanol is heated at reflux for 18 hours and then left stirring for 24 hours. The reaction mixture is concentrated under vacuum, the residue is extracted with DCM, the organic phase is washed with a saturated NaCl solution, dried over MgSO$_4$ and filtered, and the solvent is evaporated under vacuum. The residue is chromatographed on silica gel, elution being carried out with the gradient of the cyclohexane/AcOEt mixture from 80/20 (v/v) to 50/50 (v/v). 0.21 g of the expected compound is obtained, M.p.=80-83° C.

$^1$H NMR: $d_6$-DMSO (250 MHz): δ (ppm): 1.99: s: 3H; 2.02-2.16: m: 2H; 2.55: t: 2H; 4.52-4.67: m: 2H; 7.43-7.60: m: 2H; 7.77-8.01: m: 4H; 8.13-8.25: m: 1H.

EXAMPLE 4

Compound No. 18

N-(3-[3-[2-Fluoro-3-(trifluoromethyl)phenyl]-8-methoxy-4-oxocinnolin-1(4H)-yl]propyl)methanesulphonamide 0.19 g of [2-fluoro-3-(trifluoromethyl)phenyl]boronic acid is added to a solution of 0.3 g of the compound from Preparation 4.3 in 15 ml of a toluene/MeOH mixture (70/30; v/v), followed by 1.27 ml of a 2M Na$_2$CO$_3$ solution. Nitrogen is sparged into the reaction mixture for 20 minutes, 0.18 g of Tetrakis is added and the mixture is heated overnight at 75° C. The reaction mixture is filtered through Celite® the filtrate is washed with a 10% NaOH solution and with a saturated NaCl solution, the organic phase is dried over MgSO$_4$ and the solvents are evaporated under vacuum. The residue is chromatographed on silica gel, elution being carried out with the H$_2$O/MeOH mixture (50/50; v/v). 0.085 g of the expected compound is obtained, M.p.=62-64° C.

$^1$H NMR: $d_6$-DMSO) (250 MHz): δ (ppm): 1.98-2.10: m: 2H; 2.88: s: 3H; 3.00-3.10: m: 2H; 4.05: s: 3H; 4.75-4.85: m: 2H, 7.08: t: 1H; 7.50-7.60: m: 3H, 7.80-8.00: m: 3H.

EXAMPLE 5

Compound No. 33

3-(2,3-Dichorophenyl)-1-[2-(ethylsulphinyl)ethyl]-8-methoxycinnolin-4(1H)-one

A solution of 0.104 g of Compound No. 32 in 3 ml of acetic acid is cooled to 5° C., 0.03 ml of a 30% solution of H$_2$O$_2$ in water is added and the mixture is left stirring for 2 hours while allowing the temperature to rise to AT. The reaction mixture is concentrated under vacuum, the residue is extracted with DCM, the organic phase is washed with a 10% NaOH solution and with a saturated NaCl solution and dried over MgSO$_4$, and the solvent is evaporated under vacuum. 0.047 g of the expected compound is obtained after crystallization from the DCM/ether mixture, M.p.=128-130° C.

EXAMPLE 6

Compound No. 34

3-(2,3-Dichorophenyl)-1-[2-(ethylsulphonyl)ethyl]-8-methoxycinnolin-4(1H)-one

A solution of 0.245 g of 3-chloroperbenzoic acid in 5 ml of DCM is cooled to 5° C., a solution of 0.16 g of Compound No. 32 in 10 ml of DCM is added dropwise and the mixture is left stirring for 1 hour 30 minutes while allowing the temperature to rise to AT. The reaction mixture is washed with a 10% NaOH solution and with a saturated NaCl solution, the organic phase is dried over MgSO$_4$ and the solvent is evaporated under vacuum. 0.15 g of the compound is obtained, M.p.=127-129° C.

EXAMPLE 7

Compound No. 60

8-Fluoro-3-[2-fluoro-3-(trifluoromethyl)phenyl]-1-(3-methoxy-3-methylbutyl)cinnolin-4(1H)-one 0.25 g of [2-fluoro-3-(trifluoromethyl)phenyl]boronic acid is added to a solution of 0.4 g of the compound from Preparation 4.5 in 25 ml of a toluene/MeOH mixture (70/30; v/v), followed by 1.5 ml of a 2M Na$_2$CO$_3$ solution. Nitrogen is sparged into the reaction mixture for 10 minutes, 0.24 g of Tetrakis is added and the mixture is heated at 65° C. for 1 hour 30 minutes and then stirred overnight at AT. The reaction mixture is filtered through Celite® and the filtrate is concentrated under vacuum. The residue is chromatographed on silica gel, elution being carried out with the gradient of the cyclohexane/AcOEt mixture from 90/10 (v/v) and then 65/35 (v/v) up to 20/80 (v/v). 0.24 g of the expected compound is obtained.

EXAMPLE 8

Compound No. 55

N-(2-{3-[2-Fluoro-3-(trifluoromethyl)phenyl]-8-methoxy-4-oxocinnolin-1(4H)-yl}ethyl)methanesulphonamide 0.124 g of [2-fluoro-3-(trifluoromethyl)phenyl]boronic acid is added to a solution of 0.21 g of the compound from Preparation 4.6 in 12 ml of a toluene/MeOH mixture (75/25; v/v), followed by 0.74 ml of a 2M Na$_2$CO$_3$ solution. Nitrogen is sparged into the reaction mixture for 10 minutes, 0.115 g of Tetrakis is added and the mixture is heated at 65° C. for 1 hour 30 minutes. The reaction mixture is filtered through Celite® and the filtrate is concentrated under vacuum. The residue is chromatographed on silica gel, elution being carried out with the cyclohexane/AcOEt mixture (85/15; v/v) and then with AcOEt. The product obtained is taken up in an ether/DCM mixture and the precipitate formed is filtered off. 0.045 g of the expected compound is obtained.

The chemical structures and the physical properties of a few examples of compounds according to the invention, obtained by following the procedures described in the above Examples, are illustrated in the following table.

TABLE I (I)

[Structure: cinnolin-4(1H)-one core with R1 at position 3, R3 on benzene ring, and N-X-R2 at position 1]

| Compound No. | R₁ | —X—R₂ | R₃ | Salt<br>M.p. (° C.)<br>MH⁺; rt (min)<br>Conditions |
|---|---|---|---|---|
| 1 | 2-methyl-3-fluoro-6-(trifluoromethyl)phenyl | —(CH₂)₄—CH₃ | 8-OCH₃ | —<br>—<br>409; 1.99<br>C |
| 2 | 3-methyl-2-fluoro-6-(trifluoromethyl)phenyl | —(CH₂)₄—CH₃ | 8-OCH₃ | —<br>82-84<br>409; 11.07<br>B |
| 3 | 3-methyl-2-fluoro-6-(trifluoromethyl)phenyl | —(CH₂)₄—CH₃ | H | —<br>78-80<br>379; 11.07<br>A |
| 4 | 3-methyl-2-fluoro-6-(trifluoromethyl)phenyl | —(CH₂)₄—CF₃ | H | —<br>118-120<br>433; 10.47<br>A |
| 5 | 3-methyl-(trifluoromethoxy)phenyl | —(CH₂)₄—CH₃ | 8-OCH₃ | —<br>50-52<br>407; 2.24<br>C |
| 6 | 3-methyl-2-fluoro-6-(trifluoromethyl)phenyl | —(CH₂)₃—CF₃ | H | —<br>96-99<br>419; 10.22<br>A |

TABLE I-continued

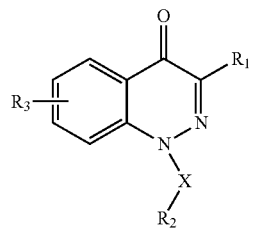

(I)

| Compound No. | R₁ | —X—R₂ | R₃ | Salt M.p. (° C.) MH⁺; rt (min) Conditions |
|---|---|---|---|---|
| 7 | 3-methyl-2-fluoro-(trifluoromethyl)phenyl | —(CH₂)₃—S—CH₃ | H | — 80-83 397; 10.08 A |
| 8 | 3-methyl-2-fluoro-(trifluoromethyl)phenyl | —(CH₂)₄—F | H | — 91-93 383; 9.74 A |
| 9 | 3-methyl-2-chloro-(trifluoromethyl)phenyl | —(CH₂)₄—CH₃ | 8-OCH₃ | — 90-91 425; 11.57 A |
| 10 | 3-methyl-(trifluoromethyl)phenyl | —(CH₂)₄—CF₃ | H | — 80-81 415; 10.94 A |
| 11 | 4-methoxy-3-methyl-fluorophenyl | —(CH₂)₄—CF₃ | H | — 97-98 395; 9.5 A |
| 12 | 3-methyl-(trifluoromethyl)phenyl | —(CH₂)₃—Cl | H | — — 367; 10.45 A |
| 13 | 3-methyl-(trifluoromethyl)phenyl | —(CH₂)₄—CH₃ | H | — 53-55 361: 18.48 A |
| 14 | 3-methyl-(trifluoromethyl)phenyl | —(CH₂)₃—S—CH₃ | H | — — 379; 10.64 A |

TABLE I-continued

Structure (I): cinnolin-4(1H)-one core with R1 at position 3, R3 on benzene ring, and N1 substituted with –X–R2.

| Compound No. | R1 | —X—R2 | R3 | Salt M.p. (° C.) MH+; rt (min) Conditions |
|---|---|---|---|---|
| 15 | 5-fluoro-2-methoxy-4-methylphenyl (F, OCH3, CH3 on phenyl) | —(CH2)3—CF3 | H | — / — / 381; 9.25 / A |
| 16 | 4-fluoro-2-methoxy-3-methylphenyl | —(CH2)3—CF3 | H | — / 118-121 / 381; 9.24 / A |
| 17 | 2-chloro-3-methyl-6-(trifluoromethyl)phenyl | —(CH2)4—CF3 | 7-Cl | — / 137-138 / 483; 1.96 / C |
| 18 | 2-fluoro-3-methyl-6-(trifluoromethyl)phenyl | —(CH2)3—NHSO2Me | 8-OCH3 | — / 62-64 / 474; 1.41 / C |
| 19 | 2-chloro-3-methyl-6-(trifluoromethyl)phenyl | —(CH2)3—NHSO2Me | 8-OCH3 | — / 95-98 / 490; 1.42 / C |
| 20 | 2-fluoro-6-methyl-3-(trifluoromethyl)phenyl | —(CH2)3—NHSO2Me | 8-OCH3 | — / 66-68 / 474; 1.31 / C |
| 21 | 2,3-dichloro-6-methylphenyl | —(CH2)3—NHSO2Me | 8-OCH3 | — / 66-68 / 456; 1.35 / C |

TABLE I-continued (I)

| Compound No. | R₁ | —X—R₂ | R₃ | Salt M.p. (° C.) MH⁺; rt (min) Conditions |
|---|---|---|---|---|
| 22 | 3-methyl-2-(trifluoromethyl)pyridin-yl | —(CH₂)₃—NHSO₂Me | 8-OCH₃ | HCl 187-189 457; 1.23 C |
| 23 | 2,3-dichloro-phenylmethyl | —(CH₂)₃—NHSO₂Me | 7-CF₃ | — 80-83 494; 1.52 C |
| 24 | 2-fluoro-3-(trifluoromethyl)phenyl-methyl | —(CH₂)₃—SO₂Me | 8-OCH₃ | — 138-139 459; 1.41 C |
| 25 | 2-fluoro-3-(trifluoromethyl)phenyl-methyl | —(CH₂)₃—NHSO₂Me | 7-CF₃ | — 128-130 512; 1.57 C |
| 26 | 3-fluoro-2-(trifluoromethyl)phenyl-methyl | —(CH₂)₃—NHSO₂Me | 7-CF₃ | — — 512; 1.49 C |
| 27 | 2-fluoro-3-(trifluoromethyl)phenyl-methyl | —(CH₂)₃—NHSO₂Me | H | — 149-152 444; 1.32 C |
| 28 | 2-(trifluoromethyl)-3-fluorophenyl-methyl | —(CH₂)₃—NHSO₂Me | 7-OCH₃ | — 54-56 |

TABLE I-continued (I)

| Compound No. | R₁ | —X—R₂ | R₃ | Salt M.p. (° C.) MH⁺; rt (min) Conditions |
|---|---|---|---|---|
| 29 | 2-fluoro-3-methyl-6-(trifluoromethyl)phenyl | —(CH₂)₂—S—CH₂—CH₃ | 8-OCH₃ | — 73-75 427; 1.92 C |
| 30 | 2-fluoro-3-methyl-6-(trifluoromethyl)phenyl | —(CH₂)₂—SO—CH₂—CH₃ | 8-OCH₃ | — 99-101 443; 1.33 C |
| 31 | 2-fluoro-3-methyl-6-(trifluoromethyl)phenyl | —(CH₂)₂—SO₂—CH₂—CH₃ | 8-OCH₃ | — 138-139 459; 1.5 C |
| 32 | 2,3-dichloro-5-methylphenyl | —(CH₂)₂—S—CH₂—CH₃ | 8-OCH₃ | — — 409; 1.89 C |
| 33 | 2,3-dichloro-5-methylphenyl | —(CH₂)₂—SO—CH₂—CH₃ | 8-OCH₃ | — 128-130 425; 1.26 C |
| 34 | 2,3-dichloro-5-methylphenyl | —(CH₂)₂—SO₂—CH₂—CH₃ | 8-OCH₃ | — 127-129 441; 1.44 C |
| 35 | 3-(trifluoromethoxy)-5-methylphenyl | —(CH₂)₃—NH—SO₂—CH₃ | 8-OCH₃ | — 98-101 472; 1.58 C |
| 36 | 2-fluoro-3-methyl-6-(trifluoromethyl)phenyl | —(CH₂)₃—NH—SO₂—CF₃ | 8-OCH₃ | — 127-130 528; 1.76 C |

TABLE I-continued
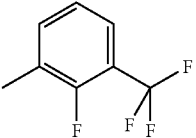
(I)
| Compound No. | R₁ | —X—R₂ | R₃ | Salt M.p. (° C.) MH⁺; rt (min) Conditions |
|---|---|---|---|---|
| 37 | 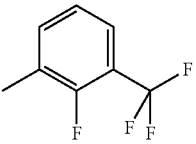 | —(CH₂)₃—NH—CO—CF₃ | 8-OCH₃ | — 51-53 492; 1.65 C |
| 38 | 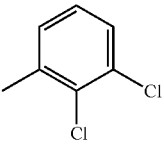 | —(CH₂)₃—NH—SO₂—CH₃ | 7-Cl | — 155-157 478; 1.5 C |
| 39 | 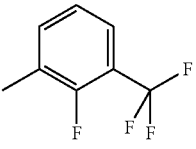 | —(CH₂)₃—N(CH₃)—SO₂—CH₃ | 8-OCH₃ | — 179-181 470; 1.51 C |
| 40 |  | —(CH₂)₂—S—CH₂—CH₃ | 8-OCF₃ | — — 481; 2.1 C |
| 41 | 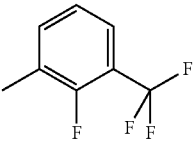 | —(CH₂)₂—S—CH₂—CH₃ | 7-Cl | — 117-119 431; 2 C |
| 42 | 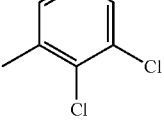 | —(CH₂)₂—SO₂—CH₂—CH₃ | 7-Cl | — 183-184 469; 1.56 C |
| 43 | 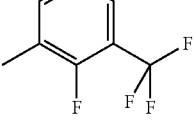 | —(CH₂)₂—S—CH₂—CH₃ | 7-Cl | — 75-77 413; 1.94 C |
| 44 |  | —(CH₂)₃—N(CH₃)—CO—CF₃ | 8-OCH₃ | — — 506; 1.77 C |

TABLE I-continued (I)

| Compound No. | R₁ | —X—R₂ | R₃ | Salt M.p. (° C.) MH⁺; rt (min) Conditions |
|---|---|---|---|---|
| 45 | 2-methyl-6-fluoro-trifluoromethylphenyl | —(CH₂)₃—NH—SO₂—CH₃ | 7-Cl | — 177-179 478; 1.41 C |
| 46 | 3-methyl-trifluoromethoxyphenyl | —(CH₂)₂—S—CH₂—CH₃ | 7-Cl | — 66-68 429; 2.11 C |
| 47 | 3-methyl-2,3-dichlorophenyl | —(CH₂)₂—SO—CH₂—CH₃ | 7-Cl | — 75-77 429; 1.34 C |
| 48 | 3-methyl-2,3-dichlorophenyl | —(CH₂)₂—SO₂—CH₂—CH₃ | 7-Cl | — 76-79 445; 1.51 C |
| 49 | 3-methyl-trifluoromethoxyphenyl | —(CH₂)₂—S—CH₂—CH₃ | 8-OCH₃ | — 86-89 425; 2.07 C |
| 50 | 3-methyl-trifluoromethoxyphenyl | —(CH₂)₂—SO₂—CH₂—CH₃ | 8-OCH₃ | — 130-132 457; 1.64 C |
| 51 | 3-methyl-2,3-dichlorophenyl | —(CH₂)₂—O—CH₂—CH₃ | 8-OCH₃ | — 134-135 393; 1.7 C |

TABLE I-continued

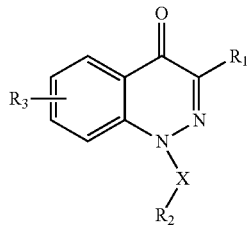

(I)

| Compound No. | R₁ | —X—R₂ | R₃ | Salt M.p. (° C.) MH⁺; rt (min) Conditions |
|---|---|---|---|---|
| 52 | 3-methyl-2-fluoro-6-(trifluoromethyl)phenyl | —(CH$_2$)$_2$—O—CH$_2$—CH$_3$ | 8-OCH$_3$ | —<br>90-93<br>411; 1.75<br>C |
| 53 | 3-methyl-2,3-dichlorophenyl | —(CH$_2$)$_3$—NH—SO$_2$—N—(CH$_3$)$_2$ | 8-OCH$_3$ | —<br>62-65<br>485; 1.51<br>C |
| 54 | 3-methyl-2-fluoro-6-(trifluoromethyl)phenyl | —(CH$_2$)$_3$—NH—SO$_2$—CHF$_2$ | 8-OCH$_3$ | —<br>—<br>510; 1.66<br>C |
| 55 | 3-methyl-2-fluoro-6-(trifluoromethyl)phenyl | —(CH$_2$)$_2$—NH—SO$_2$—CH$_3$ | 8-OCH$_3$ | 145-146<br>460; 1.73<br>C |
| 56 | 3-methyl-2-fluoro-6-(trifluoromethyl)phenyl | —(CH$_2$)$_2$—CO—N(CH$_3$)$_2$ | 8-OCH$_3$ | —<br>—<br>438; 1.73<br>C |
| 57 | 3-methyl-2-fluoro-6-(trifluoromethyl)phenyl | —(CH$_2$)$_2$—C(CH$_3$)$_2$—OCH$_3$ | 8-OCH$_3$ | —<br>—<br>439; 2.17<br>C |
| 58 | 3-methyl-2,3-dichlorophenyl | —(CH$_2$)$_2$—C(CH$_3$)$_2$—OCH$_3$ | 8-OCH$_3$ | —<br>—<br>421; 2.13<br>C |
| 59 | 3-methyl-6-fluoro-2-(trifluoromethyl)phenyl | —(CH$_2$)$_2$—C(CH$_3$)$_2$—OCH$_3$ | 8-OCH$_3$ | —<br>—<br>439; 2.07<br>C |

TABLE I-continued

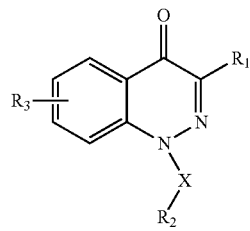

(I)

| Compound No. | R₁ | —X—R₂ | R₃ | Salt M.p. (° C.) MH⁺; rt (min) Conditions |
|---|---|---|---|---|
| 60 | (3-methyl-2-fluorophenyl-CF₂-) | —(CH₂)₂—C(CH₃)₂—OCH₃ | 8-F | —<br>—<br>427; 2.2<br>C |

The compounds according to the invention have shown a very good in vitro affinity ($IC_{50} < 500$ nM) for human and rodent $CB_2$ receptors. Affinity binding tests were carried out according to the experimental conditions described by M. Rinaldi-Carmona in J. Pharmacol. Exp. Therap., 1998, 287, 644-650, with membranes resulting either from rodent tissues or from recombinant cell lines in which human $CB_2$ receptors were expressed (Munro et al., Nature, 1993, 365, 61-65). The affinity of the compounds is expressed in the form of $IC_{50}$ (concentration causing 50% inhibition of the specific binding of the tritiated ligand used in vitro).

The compounds according to the invention have shown a modulatory effect on $CB_2$ receptors. In particular, the compounds according to the invention exhibit properties of agonist, inverse agonist and/or antagonist nature.

The agonist nature of the compounds according to the invention was demonstrated in the models of inhibition of adenylate cyclase (stimulated by forskolin) as described in M. Rinaldi-Carmona et al., J. Pharmacol. Exp. Then, 1996, 278, 871-878, and 1998, 284, 644-650, and M Bouaboula et al., J. Biol. Chem., 1997, 272, 22330-22339.

The antagonist nature of the compounds according to the invention was demonstrated in the models of reversion of the inhibition of adenylate cyclase (stimulated by forskolin) induced by an agonist of the $CB_2$ receptors as described in M. Rinaldi-Carmona et al., J. Pharmacol. Exp. Ther., 1996, 278, 871-878, and 1998, 284, 644-650.

The inverse agonist nature of the compounds according to the invention was demonstrated in the models of the activation of adenylate cyclase (stimulated by forskolin) as described in M. Portier et al., J. Pharmacol. Exp. Then, 1999, 288, 582-589.

The compounds according to the invention also have a good in vivo affinity for the $CB_2$ receptors present in the mouse spleen when they are administered orally. The tests were carried out according to the experimental conditions described by Rinaldi-Carmona et al., J. Pharmacol. Exp. Ther., 1998, 284, 644-650. The affinity of the compounds is expressed in the form of $ED_{50}$ (dose causing 50% inhibition of the specific binding of the tritiated ligand used ex vivo).

The compounds of the present invention are in particular active principles compatible with their use as medicaments and/or pharmaceutical compositions.

According to one of its aspects, the present invention relates to the use of a compound of formula (I) or of one of its pharmaceutically acceptable salts in the preparation of medicaments intended to prevent or treat any human pathology and/or for veterinary use. Thus, the compounds according to the invention can be used in man or in animals (in particular in mammals, including, without implied limitation, dogs, cats, horses, cattle or sheep) for the prevention or treatment of diseases involving $CB_2$ receptors.

Mention may be made, for example, of the following diseases or conditions:

disorders of the immune system: in particular autoimmune diseases, nonexhaustively including: psoriasis, lupus erythematosus, diseases of the connective tissue or collagen disease, Sjögren's syndrome, ankylosing spondylarthritis, rheumatoid arthritis, reactional arthritis, undifferentiated spondylarthritis, Charcot's disease, Behcet's disease, autoimmune haemolytic anaemias, multiple sclerosis, amyotropic lateral sclerosis, amyloidosis, graft rejection and diseases affecting the plasma cell line;

allergic diseases; in particular delayed or immediate hypersensitivity, asthma, allergic rhinitis, contact dermatitis and allergic conjunctivitis;

infectious parasitic, viral or bacterial diseases, including in particular AIDS and meningitis;

amyloidosis and diseases affecting the lines of the lympho-haematopoietic system;

chronic liver diseases of alcoholic origin, cirrhosis, chronic liver diseases of viral and toxic origin, and also steatohepatitis of non-alcoholic origin and primary liver cancer;

inflammatory diseases: in particular diseases of the joints: arthritis, rheumatoid arthritis, osteoarthritis, spondylitis, gout, vasculitis, Crohn's disease, inflammatory bowel disease (IBD) or irritable bowel syndrome (IBS), and acute pancreatitis ulcerative colitis;

bone diseases and osteoporosis;

pain: in particular chronic pain of inflammatory type, neuropathic pain and acute peripheral pain;

eye conditions: in particular ocular hypertension and glaucoma;

pulmonary conditions: diseases of the respiratory tract, asthma, chronic bronchitis, chronic obstructive pulmonary disease (COPD) or emphysema;
diseases of the central nervous system and neurodegenerative diseases: in particular Tourette's syndrome, Parkinson's disease, Alzheimer's disease, senile dementia, chorea, Huntington's chorea, epilepsy, psychoses, depression and spinal cord lesions.

The compound of formula (I) according to the invention can be used as medicament for the treatment or prevention of migraine, stress, diseases of psychosomatic origin, outbursts of panic attacks, epilepsy, movement disorders, dizziness, vomiting or nausea, in particular resulting from a chemotherapy;
migraine, stress, diseases of psychosomatic origin, outbursts of panic (panic attack or acute anxiety attack), epilepsy, movement disorders, dizziness, vomiting or nausea, in particular resulting from a chemotherapy;
cardiovascular diseases, in particular hypertension, arteriosclerosis, heart attack or cardiac ischaemia;
renal ischaemia;
cancers: in particular benign skin tumours, cancerous tumours and papillomas, prostate tumours, brain tumours (examples: glioblastomas, medulloepitheliomas, medulloblastomas, neuroblastomas, tumours of embryonic origin, astrocytomas, astroblastomas, ependymomas, oligodendrogliomas, plexus tumours, neuro-epitheliomas, tumour of the epiphysis, ependymoblastomas, neuroectodermal tumour, malignant meningiomas, sarcomatoses, malignant melanomas or schwannomas);
gastrointestinal disorders, diarrhoea, ulcers, bladder and urinary disorders, nephritis, disorders of endocrine origin, haemorrhagic shock, septic shock, Raynaud's syndrome and fertility disorders;
obesity, type II diabetes, metabolic syndrome, insulin resistance and adipose tissue inflammation.

More particularly, the compounds of formula (I) according to the present invention will be of use in the preparation of medicaments which make possible the prevention and/or treatment of pain, inflammatory diseases, autoimmune diseases, allergic diseases, infectious diseases, neurodegenerative diseases, cardiovascular diseases, cancers, gastrointestinal diseases, obesity, type II diabetes, insulin resistance and adipose tissue inflammation.

The use of the compounds according to the invention for the prevention and/or treatment of the abovementioned diseases and in the preparation of medicaments intended to treat these diseases forms an integral part of the invention.

The compounds of formula (I) above, or one of their pharmaceutically acceptable salts, can be used at daily doses of 0.01 to 100 mg per kilo of body weight of the mammal to be treated, preferably at daily doses of 0.1 to 50 mg/kg. In man, the dose can preferably vary from 0.1 to 4000 mg per day, more particularly from 0.5 to 1000 mg, depending on the age of the subject to be treated or the type of treatment, prophylactic or curative.

Thus, according to another of its aspects, the present invention relates to pharmaceutical compositions including, as active principle, a compound of formula (I) or one of its pharmaceutically acceptable salts and also one or more pharmaceutically acceptable excipients.

In the pharmaceutical compositions of the present invention for oral, sublingual, inhaled, subcutaneous, intramuscular, intravenous, topical, local, intratracheal, intranasal, transdermal or rectal administration, the active principles can be administered in unit administration forms, as a mixture with conventional pharmaceutical vehicles, to animals and to human beings.

The appropriate unit administration forms comprise oral forms, such as tablets, soft or hard gelatin capsules, powders, granules, oral solutions or suspensions, sublingual, buccal, intratracheal, intraocular, intranasal or inhalatory administration forms, aerosols, topical or transdermal administration forms, implants, subcutaneous, intramuscular or intravenous administration forms and rectal administration forms, For topical administration, the compounds according to the invention can be used in creams, ointments, gels or lotions.

By way of example, a unit administration form of a compound according to the invention in the tablet form can comprise the following components:

| | |
|---|---:|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |

Magnesium stearate: 3.0 mg

Orally, the dose of active principle administered per day can reach 0.01 to 100 mg/kg, taken all at once or at intervals throughout the day, preferably 0.02 to 50 mg/kg.

There may be particular cases where higher or lower dosages are appropriate; such dosages do not depart from the scope of the invention. According to the normal practice, the dosage appropriate to each patient is determined by the physician according to the method of administration and the weight and the response of the said patient.

According to another of its aspects, the present invention also relates to a method for the treatment of the pathologies indicated above which comprises the administration, to a patient, of an effective dose of a compound according to the invention or of one of its pharmaceutically acceptable salts.

The compounds according to the invention can also be used in the preparation of compositions for veterinary use.

Furthermore, the compounds according to the invention, as is or in the radiolabelled form, can be used as pharmacological tools in man or in animals for the detection and the labelling of $CB_2$ cannabinoid receptors.

The invention claimed is:

1. A compound corresponding to formula (I):

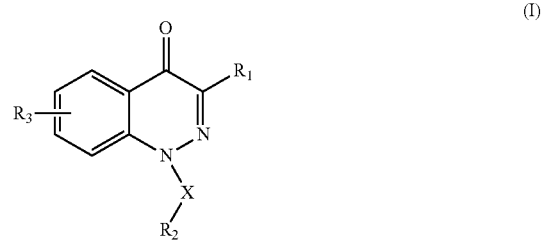

in which:
X represents a divalent $(C_2$-$C_5)$alkylene radical which is unsubstituted or substituted one or more times by an Alk group;

R₁ represents:
a phenyl which is substituted one or more times by substituents chosen independently from a halogen atom, an Alk group, an OAlk group, a cyano or an —NHSO₂Alk group;
a naphthyl which is unsubstituted or substituted one or more times by substituents chosen independently from a halogen atom, an Alk group or an OAlk group;
a pyridyl which is unsubstituted or substituted one or more times by substituents chosen independently from a halogen atom, an Alk group or an OAlk group;
a 1-benzothienyl which is unsubstituted or substituted one or more times by substituents chosen independently from a halogen atom, an Alk group or an OAlk group;
a 1,3-benzodioxolyl which is unsubstituted or substituted one or more times by substituents chosen independently from a halogen atom, an Alk group or an OAlk group;
$R_2$ represents a hydrogen atom, a halogen atom, an Alk group, an OAlk group or also a group chosen from —S-Alk, —SO-Alk, —SO₂-Alk, —CO—N(R₄)-Alk, —N(R₄)SO₂-Alk, —N(R₄)CO-Alk or —N(R₄)SO₂—N(Alk)₂;
$R_3$ represents a hydrogen atom, a halogen atom, an Alk group or an OAlk group;
$R_4$ represents a hydrogen atom or a (C₁-C₄)alkyl;
Alk represents a (C₁-C₄)alkyl which is unsubstituted or substituted one or more times by a fluorine atom;
in the form of the base or of an addition salt with an acid.

2. The compound according to claim 1, in which:
X represents a divalent (C₂-C₅)alkylene radical which is unsubstituted or substituted one or more times by an Alk group;
R₁ represents:
a phenyl which is substituted one or more times by substituents chosen independently from a halogen atom, an Alk group or an OAlk group;
a pyridyl which is substituted one or more times by substituents chosen independently from a halogen atom or an Alk group;
$R_2$ represents a hydrogen atom, a halogen atom, an Alk group, an OAlk group, an —S-Alk group, an —SO-Alk group, an —SO₂-Alk group, a —CO—N(R₄)-Alk group, an —N(R₄)SO₂-Alk group, an —N(R₄)CO-Alk group or an —N(R₄)—SO₂—N(Alk)₂ group;
$R_3$ represents a hydrogen atom, a halogen atom, an Alk group or an OAlk group;
$R_4$ represents a hydrogen atom or a (C₁-C₄)alkyl;
Alk represents a (C₁-C₄)alkyl which is unsubstituted or substituted one or more times by a fluorine atom;
in the form of the base or of an addition salt with an acid.

3. The compound according to claim 1, in which:
X represents a divalent (C₂-C₅)alkylene radical which is unsubstituted or substituted one or more times by a methyl;
R₁ represents: 3-fluoro-2-trifluoromethylphenyl, 2-fluoro-3-trifluoromethylphenyl, 3-trifluoromethoxyphenyl, 2-chloro-3-trifluoromethylphenyl, 3-trifluoromethylphenyl, 5-fluoro-2-methoxyphenyl, 4-fluoro-2-methoxyphenyl, 2,3-dichlorophenyl or 2-(trifluoromethyl)pyridin-3-yl;
$R_2$ represents a hydrogen atom, a fluorine or chlorine atom, a trifluoromethyl radical, an —OCH₃ group, an —OCH₂CH₃ group, an —S—CH₃ group, an —S—CH₂—CH₃ group, an —SO—CH₂—CH₃ group, an —SO₂CH₃ group, an —SO₂CH₂CH₃ group, an —NHSO₂—CH₃ group, an —NHSO₂—CF₃ group, an —NHSO₂CHF₂ group, an —N(CH₃)—SO₂CH₃ group, an —NH—CO—CF₃ group, an —N(CH₃)—CO—CF₃ group, an —NH—SO₂—N(CH₃)₂ group or a —CO—N(CH₃)₂ group, which are placed on the terminal position of the alkyl chain;
$R_3$ represents a hydrogen atom, a chlorine atom, a methyl group, a methoxy group or a trifluoromethyl radical;
in the form of the base or of an addition salt with an acid.

4. The compound according to claim 1 chosen from:
3-[3-Fluoro-2-(trifluoromethyl)phenyl]-8-methoxy-1-pentylcinnolin-4(1H)-one;
3-[2-Fluoro-3-(trifluoromethyl)phenyl]-8-methoxy-1-pentylcinnolin-4(1H)-one;
3-[2-Fluoro-3-(trifluoromethyl)phenyl]-1-pentylcinnolin-4(1H)-one;
3-[2-Fluoro-3-(trifluoromethyl)phenyl]-1-(5,5,5-trifluoropentyl)cinnolin-4(1H)-one;
8-Methoxy-1-pentyl-3-[3-(trifluoromethoxy)phenyl]cinnolin-4(1H)-one;
3-[2-Fluoro-3-(trifluoromethyl)phenyl]-1-(4,4,4-trifluorobutyl)cinnolin-4(1H)-one;
3-[2-Fluoro-3-(trifluoromethyl)phenyl]-1-[3-(methylthio)propyl]cinnolin-4(1H)-one;
1-(4-Fluorobutyl)-3-[2-fluoro-3-(trifluoromethyl)phenyl]cinnolin-4(1H)-one;
3-[2-Chloro-3-(trifluoromethyl)phenyl]-8-methoxy-1-pentyleinnolin-4(1H)-one;
3-[3-(Trifluoromethyl)phenyl]-1-(5,5,5-trifluoropentyl)cinnolin-4(1H)-one;
3-[2-Methoxy-5-(fluorophenyl]-1-(5,5,5-trifluoropentyl)cinnolin-4(1H)-one;
1-(3-Chloropropyl)-3-[3-(trifluoromethyl)phenyl]cinnolin-4(1H)-one;
1-Pentyl-3-[3-(trifluoromethyl)phenyl]cinnolin-4(1H)-one;
1-[3-(Methylthio)propyl]-3-[3-(trifluoromethyl)phenyl]cinnolin-4(1H)-one;
3-(4-Fluoro-2-methoxyphenyl)-1-(4,4,4-trifluorobutyl)cinnolin-4(1H)-one,
3-(5-Fluoro-2-methoxyphenyl)-1-(4,4,4-trifluorobutyl)cinnolin-4(1H)-one;
7 Chloro-3-[2-chloro-3-(trifluoromethyl)phenyl]-1-(5,5,5-trifluoropentyl)-cinnolin-4(1H)-one;
N-(3-[3-[2-Fluoro-3-(trifluoromethyl)phenyl]-8-methoxy-4-oxocinnolin-1(4H)-yl]propyl)methanesulphonamide;
N-[3-[3-[2-Chloro-3-(trifluoromethyl)phenyl]-8-methoxy-4-oxocinnolin-1(4H)-yl]propyl]methanesulphonamide;
N-[3-[3-[3-Fluoro-2-(trifluoromethyl)phenyl]-8-methoxy-4-oxocinnolin-1(4H)-yl]propyl]methanesulphonamide;
N-[3-[3-(2,3-Dichlorophenyl)-8-methoxy-4-oxocinnolin-1(4H)-yl]propyl]methanesulphonamide;
N-[3-[8-Methoxy-4-oxo-3-[2-(trifluoromethyl)pyridin-3-yl]cinnolin-1(4H)-yl]propyl]methanesulphonamide;
N-[3-[3-(2,3-Dichlorophenyl)-4-oxo-7-(trifluoromethyl)cinnolin-1(4H)-yl]propyl]methanesulphonamide;
3-[2-Fluoro-3-(trifluoromethyl)phenyl]-1-(3-(methanesulphonyl)propyl)-8-methoxy-1H-cinnolin-4-one;
N-{3-[3-[2-Fluoro-3-(trifluoromethyl)phenyl]-4-oxo-7-trifluoromethyl-4H-cinnolin-1-yl]propyl}methanesulphonamide;
N-{3-[3-[3-Fluoro-2-(trifluoromethyl)phenyl]-4-oxo-7-trifluoromethyl-4H-cinnolin-1-yl]propyl}methanesulphonamide;

N-{3-[3-[2-Fluoro-3-(trifluoromethyl)phenyl]-4-oxo-4H-cinnolin-1-yl]-propyl}methanesulphonamide;
N-{3-[3-[2-Fluoro-3-(trifluoromethyl)phenyl]-7-methoxy-4-oxo-4H-cinnolin-1-yl]propyl}methanesulphonamide;
1-[2-(Ethylthio)ethyl]-3-[2-fluoro-3-(trifluoromethyl)phenyl]-8-methoxycinnolin-4(1H)-one;
1-[2-(Ethylsulphinyl)ethyl]-3-[2-fluoro-3-(trifluoromethyl)phenyl]-8-methoxycinnolin-4(1H)-one;
1-[2-(Ethylsulphonyl)ethyl]-3-[2-fluoro-3-(trifluoromethyl)phenyl]-8-methoxycinnolin-4(1H)-one;
3-(2,3-Dichlorophenyl)-1-[2-(ethylthio)ethyl]-8-methoxycinnolin-4(1H)-one;
3-(2,3-Dichlorophenyl)-1-[2-(ethylsulphinyl)ethyl]-8-methoxycinnolin-4(1H)-one;
3-(2,3-Dichlorophenyl)-1-[2-(ethylsulphonyl)ethyl]-8-methoxycinnolin-4(1H)-one;
N-(3-{8-Methoxy-4-oxo-3-[3-(trifluoromethoxy)phenyl]cinnolin-1(4H)-yl}propyl)methanesulphonamide;
1,1,1-Trifluoro-N-(3-{3-[2-fluoro-3-(trifluoromethyl)phenyl]-8-methoxy-4-oxocinnolin-1(4H)-yl}propyl)methanesulphonamide;
2,2,2-Trifluoro-N-(3-{3-[2-fluoro-3-(trifluoromethyl)phenyl]-8-methoxy-4-oxocinnolin-1(4H)-yl}propyl)acetamide;
N-(3-{7-Chloro-3-[2-fluoro-3-(trifluoromethyl)phenyl]-4-oxocinnolin-1(4H)-yl}propyl)methanesulphonamide;
N-{3-[3-(2,3-Dichlorophenyl)-8-methoxy-4-oxocinnolin-1(4H)-yl]propyl}-N-methylmethanesulphonamide;
1-[2-(Ethylthio)ethyl]-3-[2-fluoro-3-(trifluoromethyl)phenyl]-8-(trifluoromethoxy)cinnolin-4(1H)-one;
7-Chloro-1-[2-(ethylthio)ethyl]-3-[2-fluoro-3-(trifluoromethyl)phenyl]cinnolin-4(1H)-one;
7-Chloro-1-[2-(ethylsulphonyl)ethyl]-3-[2-fluoro-3-(trifluoromethyl)phenyl]cinnolin-4(1H)-one;
7-Chloro-3-(2,3-dichlorophenyl)-1-[2-(ethylthio)ethyl]cinnolin-4(1H)-one;
2,2,2-Trifluoro-N-(3-{3-[2-fluoro-3-(trifluoromethyl)phenyl]-8-methoxy-4-oxocinnolin-1(4H)-yl}propyl)-N-methylacetamide;
N-(3-{7-Chloro-3-[3-fluoro-2-(trifluoromethyl)phenyl]-4-oxocinnolin-1(4H)-yl}propyl)methanesulphonamide;
7-Chloro-1-[2-(ethylthio)ethyl]-3-[3-(trifluoromethoxy)phenyl]cinnolin-4(1H)-one;
7-Chloro-3-(2,3-dichlorophenyl)-1-[2-(ethylsulphinyl)ethyl]cinnolin-4(1H)-one;
7-Chloro-3-(2,3-dichlorophenyl)-1-[2-(ethylsulphonyl)ethyl]cinnolin-4(1H)-one;
1-[2-(Ethylthio)ethyl]-8-methoxy-3-[3-(trifluoromethoxy)phenyl]cinnolin-4(1H)-one;
1-[2-(Ethylsulphonyl)ethyl]-8-methoxy-3-[3-(trifluoromethoxy)phenyl]cinnolin-4(1H)-one;
3-(2,3-Dichlorophenyl)-1-(2-ethoxyethyl)-8-methoxycinnolin-4(1H)-one;
1-(2-Ethoxyethyl)-3-[2-fluoro-3-(trifluoromethyl)phenyl]-8-methoxycinnolin-4(1H)-one;
N'-{3-[3-(2,3-Dichlorophenyl)-8-methoxy-4-oxocinnolin-1(4H)-yl]propyl}-N,N-dimethylsulphamide;
1,1-Difluoro-N-(3-{3-[2-fluoro-3-(trifluoromethyl)phenyl]-8-methoxy-4-oxocinnolin-1(4H)-yl}propyl)methanesulphonamide;
N-(2-{3-[2-Fluoro-3-(trifluoromethyl)phenyl]-8-methoxy-4-oxocinnolin-1(4H)-yl}ethyl)methanesulphonamide;
3-{3-[2-Fluoro-3-(trifluoromethyl)phenyl]-8-methoxy-4-oxocinnolin-1(4H)-yl}-N,N-dimethylpropanamide;
3-[2-Fluoro-3-(trifluoromethyl)phenyl]-8-methoxy-1-(3-methoxy-3-methylbutyl)cinnolin-4(1H)-one;
3-(2,3-Dichlorophenyl)-8-methoxy-1-(3-methoxy-3-methylbutyl)cinnolin-4(1H)-one;
3-[3-Fluoro-2-(trifluoromethyl)phenyl]-8-methoxy-1-(3-methoxy-3-methylbutyl)cinnolin-4(1H)-one;
8-Fluoro-3-[2-fluoro-3-(trifluoromethyl)phenyl]-1-(3-methoxy-3-methylbutyl)cinnolin-4(1H)-one;

in the form of the base or of an addition salt with an acid.

5. A pharmaceutical composition comprising the compound of claim 1, and pharmaceutically acceptable salts thereof.

6. The pharmaceutical composition of claim 5, further comprising at least one pharmaceutically acceptable excipient.

7. A process for preparing the compound of claim 1, comprising reacting
a compound of formula:

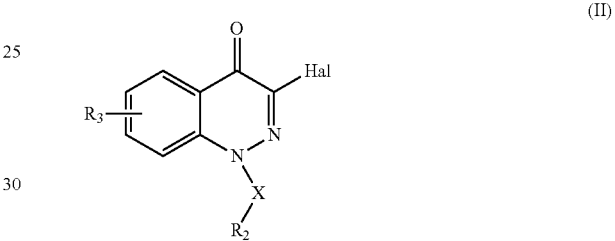

(II)

in which X, $R_2$ and $R_3$ are as defined for a compound of formula (I) in claim 1 and Hal represents a halogen atom, in the presence of a base with a compound of formula:

$R_1$—B(OH)$_2$ (III)

in which $R_1$ is as defined for a compound of formula (I) in claim 1.

8. A process for preparing the compound of claim 1 in which $R_2$ represents an —S-Alk group comprising reacting a compound of formula:

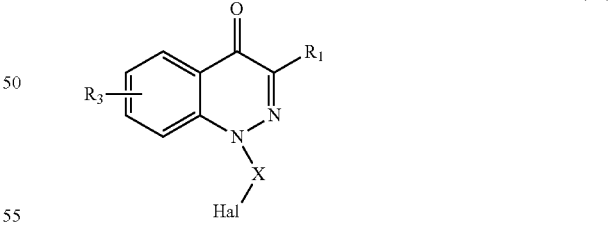

(IV)

in which X, $R_1$ and $R_3$ are as defined for a compound of formula (I) in claim 1 and Hal represents a halogen atom, in the presence of a base with a sodium alkanethiolate derivative of formula:

NaS-Alk (V)

in which Alk is as defined for a compound of formula (I) in claim 1.

* * * * *